United States Patent
Theelke et al.

(10) Patent No.: US 11,180,417 B2
(45) Date of Patent: Nov. 23, 2021

(54) ZIRCONIA ARTICLE WITH HIGH ALUMINA CONTENT, PROCESS OF PRODUCTION AND USE THEREOF

(71) Applicant: 3M INNOVATIVE PROPERTIES COMPANY, St. Paul, MN (US)

(72) Inventors: Bjorn Theelke, Landsberg am Lech (DE); Rainer K. Dittmann, Munich (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/484,858

(22) PCT Filed: Feb. 8, 2018

(86) PCT No.: PCT/US2018/017332
§ 371 (c)(1),
(2) Date: Aug. 9, 2019

(87) PCT Pub. No.: WO2018/151995
PCT Pub. Date: Aug. 23, 2018

(65) Prior Publication Data
US 2020/0055779 A1 Feb. 20, 2020

(30) Foreign Application Priority Data
Feb. 15, 2017 (EP) .................................. 17156204

(51) Int. Cl.
*C04B 35/488* (2006.01)
*A61C 13/083* (2006.01)
(Continued)

(52) U.S. Cl.
CPC ...... *C04B 35/4885* (2013.01); *A61C 13/0022* (2013.01); *A61C 13/082* (2013.01);
(Continued)

(58) Field of Classification Search
CPC .......................... C04B 35/4885; A61C 13/083
See application file for complete search history.

(56) References Cited

U.S. PATENT DOCUMENTS

| 4,575,330 A | 3/1986 | Hull |
| 4,820,666 A | 4/1989 | Hirano |
(Continued)

FOREIGN PATENT DOCUMENTS

| EP | 1580178 | 9/2005 |
| JP | 05301767 | 11/1993 |
(Continued)

OTHER PUBLICATIONS

International Search report for PCT International Application No. PCT/US2018/017332 dated May 25, 2018, 5 pages.

*Primary Examiner* — Karle E Group
(74) *Attorney, Agent, or Firm* — Ashley M. Dreis; 3M Innovative Properties Company

(57) ABSTRACT

The invention relates to a porous zirconia article in particular for use in the dental or orthodontic field, the porous zirconia article comprising $ZrO_2$: 80 to 87 wt. %, $Y_2O_3$: 3 to 5 wt. %, $Al_2O_3$: 10 to 14 wt. %, wt. % with respect to the weight of the porous zirconia article, the porous zirconia article being characterized by a BET surface from 15 to 100 $m^2/g$. The invention also relates to a sintered zirconia article in particular for use in the dental or orthodontic field, the sintered zirconia article comprising $ZrO_2$: 80 to 87 wt. %, $Y_2O_3$: 3 to 5 wt. %, $Al_2O_3$: 10 to 14 wt. %, wt. % with respect to the weight of the porous zirconia article, the sintered zirconia article being characterized by a corundum crystal phase content of 7 to 12 wt. % and a flexural strength of at least 2,000 MPa.

9 Claims, 1 Drawing Sheet

(51) Int. Cl.

| | |
|---|---|
| B33Y 10/00 | (2015.01) |
| B33Y 70/00 | (2020.01) |
| A61K 6/807 | (2020.01) |
| A61K 6/822 | (2020.01) |
| A61K 6/818 | (2020.01) |
| A61C 13/00 | (2006.01) |
| A61C 13/08 | (2006.01) |
| B28B 1/00 | (2006.01) |
| B28B 1/14 | (2006.01) |
| B28B 11/24 | (2006.01) |
| C04B 35/624 | (2006.01) |
| C04B 35/634 | (2006.01) |
| C04B 35/64 | (2006.01) |
| B33Y 80/00 | (2015.01) |

(52) U.S. Cl.
CPC ............ *A61C 13/083* (2013.01); *A61K 6/807* (2020.01); *A61K 6/818* (2020.01); *A61K 6/822* (2020.01); *B28B 1/001* (2013.01); *B28B 1/14* (2013.01); *B28B 11/243* (2013.01); *B33Y 10/00* (2014.12); *B33Y 70/00* (2014.12); *C04B 35/624* (2013.01); *C04B 35/634* (2013.01); *C04B 35/64* (2013.01); *A61C 2201/002* (2013.01); *B33Y 80/00* (2014.12); *C04B 2235/3206* (2013.01); *C04B 2235/3208* (2013.01); *C04B 2235/3217* (2013.01); *C04B 2235/3225* (2013.01); *C04B 2235/3227* (2013.01); *C04B 2235/3229* (2013.01); *C04B 2235/3246* (2013.01); *C04B 2235/6026* (2013.01); *C04B 2235/762* (2013.01); *C04B 2235/765* (2013.01); *C04B 2235/77* (2013.01); *C04B 2235/785* (2013.01); *C04B 2235/9646* (2013.01)

(56) References Cited

U.S. PATENT DOCUMENTS

| | | | |
|---|---|---|---|
| 6,283,997 | B1 | 9/2001 | Garg |
| 7,429,422 | B2 | 9/2008 | Davidson |
| 8,003,040 | B2 | 8/2011 | El-Siblani |
| 2015/0118648 | A1* | 4/2015 | Johannes ................ A61L 27/10 |
| | | | 433/199.1 |
| 2015/0125821 | A1* | 5/2015 | Theelke ................ A61K 6/818 |
| | | | 433/201.1 |
| 2015/0203650 | A1 | 7/2015 | Kolb |
| 2017/0362129 | A1* | 12/2017 | Hirota ................ C04B 35/6262 |

FOREIGN PATENT DOCUMENTS

| | | |
|---|---|---|
| JP | 2010-248051 | 11/2010 |
| WO | WO 2006-024098 | 3/2006 |
| WO | WO 2008-040815 | 4/2008 |
| WO | WO 2009-085926 | 7/2009 |
| WO | WO 2013-055432 | 4/2013 |
| WO | WO 2013-191754 | 12/2013 |
| WO | WO 2015-148215 | 10/2015 |
| WO | WO 2016-140840 | 9/2016 |

\* cited by examiner

ZIRCONIA ARTICLE WITH HIGH ALUMINA CONTENT, PROCESS OF PRODUCTION AND USE THEREOF

CROSS REFERENCE TO RELATED APPLICATIONS

This application is a national stage filing under 35 U.S.C. 371 of PCT/US2018/017332, filed Feb. 8, 2018, which claims the benefit of EP Application No. 17156204.4, filed Feb. 15, 2017, the disclosure of each of which is incorporated herein by reference in its entirety.

FIELD OF THE INVENTION

The invention relates to a porous zirconia article with a comparably high content of alumina, a sintered zirconia article made therefrom and processes for producing such articles. The zirconia article is in particular useful in the dental and orthodontic field.

BACKGROUND

Zirconia ceramic materials, in particular for use in the dental or orthodontic field, need to be sufficiently tough and also need to be sufficiently hydrothermal stable.

According to the phase diagram and depending on temperature, pure zirconia can exist in different crystal phases.

The transformation from one phase to the other typically goes along with a change in volume which may lead to a destruction of the zirconia ceramic article after sintering.

To address this issue, zirconia ceramics for technical use are typically provided in a stabilized form, e.g. by adding $Y_2O_3$ or CaO.

Depending on the $Y_2O_3$ content, yttria stabilized zirconia (Y-TZP) can show a wide range of properties.

Y-TZP with an $Y_2O_3$ content below 3 mol % typically shows high strength and fracture toughness but is said to be also sensitive to low temperature aging.

The transformation of tetragonal to monoclinic crystal phase under influence of humidity and temperature typically leads to a decrease of mechanical properties, which makes those compositions unsuitable for medical or industrial applications.

To address this issue, it has been suggested to add second phases to Y-TZP having an yttria content below 3 mol %. It is assumed that this may contribute to reduce the aging sensitivity and preserve high mechanical properties. In this respect, the addition of alumina was found to be useful.

Alumina toughened zirconia (ATZ) is typically produced by compressing zirconia powders containing alumina followed by a hot isostatic pressing step.

JP 2010/248051 A1 (JAPAN MEDICAL MATERIALS) relates to an alumina-zirconia composite sintered compact exhibiting high strength and high fracture toughness and also simultaneously satisfying the stabilization of a crystal phase, and exhibiting stability over a long period of time when the compact is used as a living body member of an artificial joint for example. The alumina-zirconia composite sintered compact includes α-alumina, Si-containing α-alumina, strontium aluminate, tetragonal zirconia and monoclinic zirconia.

WO 2008/040815 A1 (Vita Zahnfabrik) describes a sintered material comprising a) from 98-50 vol. % zirconia as matrix, i) stabilized with a stabilizing composition having ii) of from 2 to 3 mol. % ytrria and of from 10 to 15 mol. % ceria, wherein the term mole percent is related to the zirconia matrix and iii) the stabilizing composition is present in the range of from 1:99 to 99:1 and b) from 2 to 50 vol. % alumina of which from 5 to 90 vol. % is in the form of hexagonal platelets of general formula REA1 11018, where RE stands for rare earth metal.

WO 2006/24098 A1 (Advanced Nanotechnology) describes a multi-component powder for consolidation to form a sinterable green body for a zirconia ceramic. The multi-component powder comprises at least 80 vol. % of nano-sized particles of zirconia and up to 20 vol. % of a stabilizing agent which may form a coating around the nano-sized particles of zirconia.

EP 1 580 178 A1 (Matsushita Electric Works) describes a $ZrO_2$—$Al_2O_3$ composite ceramic material having excellent wear resistance, hardness, strength and toughness. The ceramic material comprises a ZrO2 phase composed of 90 vol. % or more of tetragonal $ZrO_2$ and preferably containing 10 to 12 mol. % of $CeO_2$ as a stabilizer and an $Al_2O_3$ phase. An amount of the $Al_2O_3$ phase in the ceramic material is in a range of 20 to 70 vol. %.

JP 05-301767/JP 3157600 B2 (Nisshin Flour Milling) describes a multiple sintered compact which is said to have improved flexural strength and fracture toughness. The compact comprises ceria-stabilized zirconia, alpha-alumina and lanthanum-based beta-alumina.

WO 2013/055432 A1 (3M) describes aerogels, calcined articles and crystalline articles comprising $ZrO_2$. Exemplary uses of the crystalline metal oxide articles include dental articles and orthodontic appliances.

US 2015/0125821 A1 (Theelke et al.) describes a process for producing a zirconia based dental implant by conducting a two surface treatment step. As a specific example of an alumina toughened zirconia material a composition is described comprising 3 to 6 wt. % $Y_2O_3$, 10 to 30 wt. % $Al_2O_3$ and 87 to 64 wt. %. A powder composition falling within these ranges is commercially available from Tosoh Corporation under the designation TZ3YS20AB.

SUMMARY OF THE INVENTION

However, there is still a need for a hydrothermal stable zirconia material with beneficial mechanical properties, like high fracture strength and/or toughness.

It would also be desirable, if such a zirconia material can be produced effectively, e.g. without the need for conducting a hot isostatic pressing step.

It would also be desirable, if the zirconia material can be obtained by a casting or an additive-manufacturing process.

It would also be desirable to have a material at hand, which allows the production of thin walled geometrically complex articles.

At least one or more of the above-mentioned objects can be solved by the articles and processes described in the present text.

In one embodiment, the invention features a porous zirconia article as described in the present text, in particular for use in the dental or orthodontic field, the porous zirconia article comprising $ZrO_2$: 80 to 87 wt. %,
$Y_2O_3$: 3 to 5 wt. %,
$Al_2O_3$: 10 to 14 wt. %, wt. % with respect to the weight of the porous zirconia article, the porous zirconia article being characterized by the following parameters alone or in combination:

a) density: from 40 to 60% of theoretical density;
b) average connected pore diameter: from 2 to 100 nm;

c) BET surface: from 11 to 100 m²/g or from 15 to 100 m²/g;
d) Vickers hardness: from 10 to 100 HV1.

A further embodiment of the invention is directed to a sintered zirconia article as described in the present text, in particular for use in the dental or orthodontic field, the sintered zirconia article comprising $ZrO_2$: 80 to 87 wt. %,
$Y_2O_3$: 3 to 5 wt. %,
$Al_2O_3$: 10 to 14 wt. %, wt. % with respect to the weight of the porous zirconia article, the sintered zirconia article being characterized by a corundum crystal phase content of than 7 to 12 wt. % and a flexural strength of at least 2,000 MPa.

The invention is also related to a process of producing a porous zirconia article as described in the present text in particular for use in the dental or orthodontic field, the process comprising the steps of a) providing a composition comprising
   $ZrO_2$ in the term of inorganic oxide: 80 to 87 wt. %,
   $Y_2O_3$ in the term of inorganic oxide: 3 to 5 wt. %,
   $Al_2O_3$ in the term of inorganic oxide: 10 to 14 wt. %,
wt. % with respect to the weight of the whole composition,
b) processing the composition by either a casting technique or an additive manufacturing technique,
c) applying a calcining step.

Figure 1:
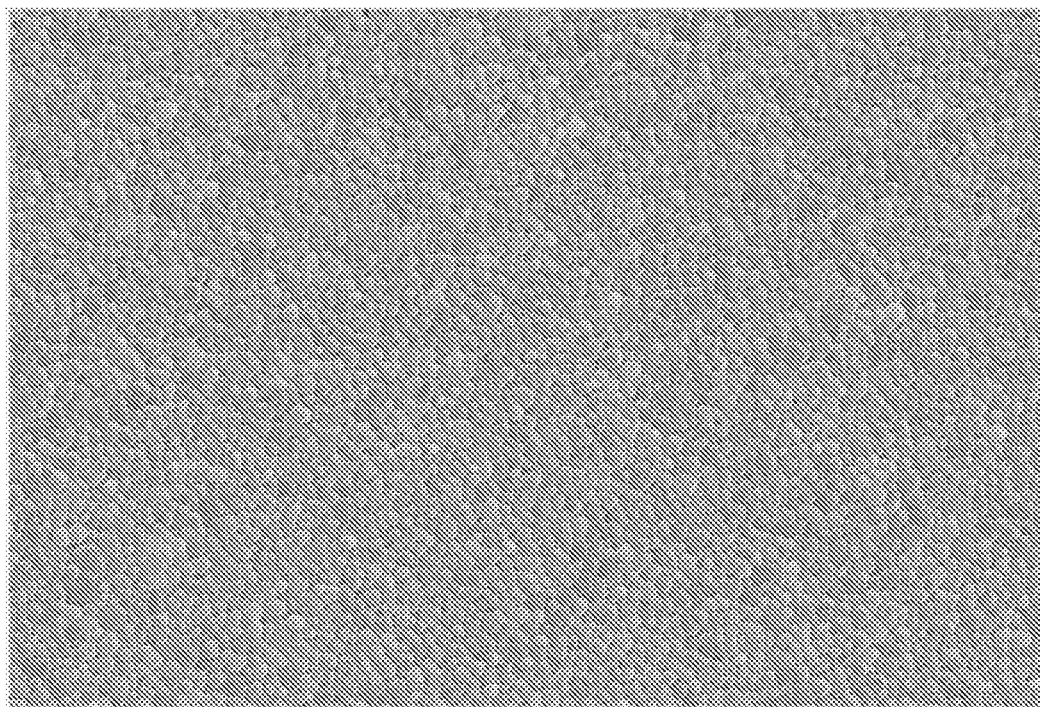
FIG. 1 shows the microstructure of a 3Y-TZP reference material.

Unless defined differently, for this description the following terms shall have the given meaning:

The term "dental article" means any article which is to be used in the dental field, especially for producing a dental restoration.

Examples of dental articles include crowns, bridges, inlays, onlays, veneers, facings, copings, crown and bridged framework, implants, abutments, dental milling blocks, monolithic dental restorations and parts thereof.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

The term "orthodontic article" means any article which is to be used in the orthodontic field.

Examples of orthodontic articles include brackets, buccal tubes, cleats and buttons and parts thereof.

A dental or orthodontic article should not contain components which are detrimental to the patient's health and thus free of hazardous and toxic components being able to migrate out of the dental or orthodontic article. The surface of a tooth is considered not to be a dental or orthodontic article.

By "dental mill blank" is meant a solid block (3-dim article) of material from which a dental article, dental workpiece, dental support structure or dental restoration can and typically is to be machined in a subtractive process, e.g. besides milling also by grinding, drilling etc.

A dental mill blank has a geometrically defined shape and comprises at least one flat surface. A so-called "free form surface" is not regarded as "geometrically defined". In this respect, the shape of a dental restoration (e.g. crown or bridge) itself is not regarded as a dental mill blank.

"Zirconia article" shall mean a 3-dimensional (3-dim) article wherein at least one of the x, y, z dimensions is at least 1 mm, at least 0.5 mm, at least 0.25 mm, the article being comprised of at least about 80 or at least about 82 or at least about 85 wt. % zirconia.

"Ceramic" or "ceramic article" means a non-metallic material that is produced by application of heat. Ceramics are usually hard, and brittle and, in contrast to glasses or glass ceramics, display an essentially purely crystalline structure. Ceramics are usually classified as inorganic materials.

"Crystalline" means a solid composed of atoms arranged in a pattern periodic in three dimensions (i.e., has long-range crystal structure as determined by X-ray diffraction).

A "crystallite" means a crystalline domain of a solid having a defined crystal structure. A crystallite can only have one crystal phase.

"Additive manufacturing" means processes used to make 3-dimensional articles. An example of an additive manufacturing technique is stereolithography (SLA) in which successive layers of material are laid down under computer control. The articles can be of almost any shape or geometry and are produced from a 3-dimensional model or other electronic data source.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. The material or article described in the present text does not contain a glass.

"Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and more traditional crystalline ceramics. It is formed as a glass, and then made to crystallize partly by heat treatment. Glass ceramics may refer to a mixture of lithium-, silicon- and aluminium oxides. The material or article described in the present text does not contain a glass-ceramic.

"Sol" refers to a continuous liquid phase containing discrete particles having sizes in a range from 1 nm to 100 nm or from 1 to 50 nm, a so-called "colloidal solution". The sols described in the present text are translucent and do show a so-called "Tyndall effect" or "Tyndall scattering". The size of the particles is below the wavelength of the visible light (400 to 750 nm).

A transparent material lets light pass through according to Snell's law (classical law of refraction). So, a picture can be seen in its details through a platelet of a transparent material.

A translucent material lets light partially permeate through although it is not fully transparent, i.e. showing a significant volume scattering of the transmitted light. The reciprocal property of translucency is opacity (O). $O=1/T=I/I0$ (T=Transmission, I=Intensity of permeated light, I=Intensity of light before permeation). So, opacity values smaller than about 0.9 for a 1 mm thick platelet with a diameter of 15 mm are regarded as translucent (e.g. for a measurement with a Color i7 device, X-Rite corporation USA, measurement mode: remission contrast ratio).

Opacity can be measured by various means: in transmission, in remission, in remission using the contrast ratio method.

By "machining" is meant milling, grinding, cutting, carving, or shaping a material by a machine. Milling is usually faster and more cost effective than grinding. A "machinable article" is an article having a 3-dim shape and having sufficient strength to be machined.

A "powder" means a dry, bulk material composed of a large number of fine particles that may flow freely when shaken or tilted.

A "particle" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

The term "associated" refers to a grouping of two or more primary particles that are aggregated and/or agglomerated. Similarly, the term "non-associated" refers to two or more primary particles that are free or substantially free from aggregation and/or agglomeration.

The term "aggregation" refers to a strong association of two or more primary particles. For example, the primary particles may be chemically bound to one another. The breakdown of aggregates into smaller particles (e.g., primary particles) is generally difficult to achieve.

The term "agglomeration" refers to a weak association of two or more primary particles. For example, particles may be held together by charge or polarity. The breakdown of agglomerates into smaller particles (e.g., primary particles) is less difficult than the breakdown of aggregates into smaller particles.

The term "primary particle size" refers to the size of a non-associated single crystal zirconia particle, which is considered to be a primary particle. X-ray diffraction (XRD) is typically used to measure the primary particle size.

"Soluble" means that a component (solid) can be completely dissolved within a solvent. That is, the substance is able to form individual molecules (like glucose) or ions (like sodium chloride) or non-settling particles (like a sol) when dispersed in water at 23° C. The solution process, however, might take some time, e.g. stirring the composition over a couple of hours (e.g. 10 or 20 h) might be required.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of a material sample can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics. Accordingly, an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured on different material samples (e.g. using a mercury "Poremaster 60-GT" from Quantachrome Inc., USA) according to DIN 66133. A material having an open-celled or open-porous structure can be passed through by e.g. gases.

The "average connected pore diameter" means the average size of the open-celled pores of a material. The average connected pore diameter can be calculated as described in the Examples section.

The term "calcining" or "debindering" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size. "Green body gel" means a three-dim gel resulting from the curing reaction of polymerizable components contained in a sol, including organic binder and solvent.

"Aerogel" means a three-dimensional low-density (e.g., less than 30% of theoretical density) solid. An aerogel is a porous material derived from a green body gel, in which the liquid component of the gel has been replaced with a gas. The solvent removal is often done under supercritical conditions. During this process, the network does not substantially shrink and a highly porous, low-density material can be obtained.

A "green body" means an un-sintered ceramic item, typically having an organic binder present.

A "white body" means a pre-sintered ceramic item.

A "geometrically defined article" means an article the shape of which can be described with geometrical terms including 2-dimensional terms like circle, square, rectangle, and 3-dimensional terms like layer, cube, cuboid, sphere.

A material or composition is "essentially or substantially free of" a certain component within the meaning of the invention, if the material or composition does not contain said component as an essential feature. Thus, said component is not willfully added to the composition or material either as such or in combination with other components or ingredient of other components. A composition or material being essentially free of a certain component usually contains the component in an amount of less than about 1 wt. % or less than about 0.1 wt. % or less than about 0.01 wt. % (or less than about 0.05 mol/l solvent or less than about 0.005 mol/l solvent or less than about 0.0005 mol/l solvent) with respect to the whole composition or material. Ideally the composition or material does not contain the said component at all. However, sometimes the presence of a small amount of the said component is not avoidable e.g. due to impurities.

As used herein, "a", "an", "the", "at least one" and "one or more" are used interchangeably. The terms "comprise" or "contain" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.). Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

DETAILED DESCRIPTION

The invention described in the present text provides a couple of advantages.

The invention provides a zirconia article with good mechanical properties.

A zirconia article which can be obtained from the porous zirconia article described in the present text shows a flexural strength of more than 2,000 MPa and a fracture toughness of more than 8 MPa*m$^{0.5}$ after sintering, even without applying a hot isostatic pressing step (HIP).

Further, it was found that that the material described in the present text is sufficiently hydrothermal stable, i.e. showing only a reduced or limited phase transformation, if the material is stored in water at elevated temperature.

These strength and toughness values are higher than the values reported for commercially available ceramic materials developed for medical and industrial applications.

Zirconia stabilized with e.g. 2.2 mol % yttria typically has a flexural strength in the range of 1,800 MPa and a fracture toughness of 8 MPa*m$^{0.5}$. However, such a material is not sufficiently hydrothermal stable to make it useful in the dental and/or orthodontic field.

On the other hand, zirconia stabilized with e.g. 3 mol % yttria (3Y-TZP) is sufficiently hydrothermal stable, but has a lower flexural strength in the range of 1.400 MPa and a fracture toughness of 7 MPa*m$^{0.5}$. The hydrothermal stability can be improved, if alumina is added.

E.g., it was found that adding alumina in an amount of 5 wt. % to zirconia stabilized with 2.2 mol % yttria resulted in a sufficiently hydrothermal stable ceramic without affecting the mechanical and optical properties.

It was assumed that addition of alumina will not lead to an increase in strength, since the alumina phase does not have transformation toughening properties like zirconia which has been partially stabilized with yttria.

However, surprisingly it was found that increasing the alumina content lead to a further increase in strength by more than 40% compared to commercially available 3Y-TZP materials (having a strength in the range of about 1,400 MPa).

As outlined above, ceramic materials having a strength levels above 2,000 MPa are typically produced by compacting powder and conducting a hot isostatic pressing step.

Such a step is not needed, if the composition described in the present text is used, having a comparably low yttria content combined with a comparably high alumina content.

Without wishing to be bound to a certain theory, a possible mechanism for the increase in strength observed for the zirconia material described in the present text could be the difference in the coefficient of thermal expansion between zirconia and alumina that may lead to internal material matrix stresses during cooling after sintering.

Additionally, the porous zirconia article described in the present text can be produced by applying near net shape forming processes, including additive manufacturing techniques and direct casting or moulding techniques.

This enables an effective production process compared to existing processes where the desired article is machined out of a larger milling block.

However, if desired it is also possible to produce the zirconia articles by a subtractive process, e.g. by machining the desired zirconia article out of a milling block, either in pre-sintered or finally sintered stage.

Further, the combination of high strength material and the possibility of using near net shape forming processes allows the production of thin walled or small sized components with complex geometries for high load bearing medical applications (e.g. pediatric dental crowns, implants, brackets) or tools and components for improving industrial processes (technical cutting, sealing, forming, wire drawing, components for pumps).

Thus, the present invention provides a ceramic material having good physical properties, like high strength, sufficient toughness combined with sufficient hydrothermal stability and opacity.

According to one embodiment the invention relates to a porous zirconia article in particular for use in the dental or orthodontic field.

The porous zirconia article has the following composition:
 $ZrO_2$: 80 to 87 wt. %,
 $Y_2O_3$: 3 to 5 wt. %,
 $Al_2O_3$: 10 to 14 wt. %,
wt. % with respect to the weight of the porous zirconia article.

As the chemical behavior of $ZrO_2$ and $HfO_2$ is pretty similar and in view of the fact that it is very difficult to separate $HfO_2$ from $ZrO_2$, the porous zirconia article may contain small amounts of $HfO_2$, too, e.g. up to 4.5 mol %. If $HfO_2$ is present, it is not separately listed but encompassed in the amount given for ZrO2. Thus, $ZrO_2$ stands for $ZrO_2$ and $HfO_2$.

The porous zirconia article does typically not comprise either of the following components alone or in combination:
 CaO in an amount above 1 wt. %;
 MgO in an amount above 1 wt. %;
 $CeO_2$ in an amount above 1 wt. %;
 $La_2O_3$ in an amount above 1 wt. %;
wt. % with respect to the weight of the porous zirconia article.

Thus, the porous zirconia article is typically essentially free of those components.

The presence of the above components is not desired and may negatively influence mechanical properties.

The porous zirconia article can typically be characterized by the following parameters alone or in combination:
 a) density: from 40 to 60% of theoretical density;
 b) average connected pore diameter: from 2 to 100 nm or from 2 to 80 nm or from 4 to 50 nm or from 4 to 30 nm or from 4 to 25 nm;

c) BET surface: from 11 to 100 m²/g or from 15 to 100 m²/g or from 16 to 60 m²/g or from 16 to 30 m²/g;
d) Vickers hardness: from 10 to 100 HV1.
HV1 means that the test force applied was 9.807 N.
Sometimes, a combination of parameters a) and b) or b) and c) or c) and d) can be preferred.

A BET surface in the above-mentioned range is often beneficial, because it facilitates the sintering step. Particularly, it may enable the sintering of the zirconia article to final density without applying further pressure or heat.

Porous zirconia articles obtained from processing commercially available zirconia powders like TZ3YS20AB (Tosoh Corporation) have a BET surface which is below 15 m²/g, typically in a range of 4 to 6 m²/g.

Further, the porous zirconia article can also be characterized by the following parameters alone or in combination:
a) showing a $N_2$ adsorption and/or desorption isotherm with a hysteresis loop;
b) showing a $N_2$ adsorption and desorption of isotherm type IV according to IUPAC classification and a hysteresis loop;
c) showing a $N_2$ adsorption and desorption isotherm of type IV with a hysteresis loop of type H1 according to IUPAC classification;
d) showing a $N_2$ adsorption and desorption isotherm of type IV with a hysteresis loop of type H1 according to IUPAC classification in a p/p0 range of 0.70 to 0.99.

According to a further embodiment the invention relates to a sintered zirconia article.

With respect to the chemical composition, the sintered zirconia article is essentially identical to the chemical composition of the porous zirconia article.

The sintered zirconia article comprises:
$ZrO_2$: 80 to 87 wt. %,
$Y_2O_3$: 3 to 5 wt. %,
$Al_2O_3$: 10 to 14 wt. %,
wt. % with respect to the weight of the porous zirconia article.

The sintered zirconia article is characterized by a corundum crystal phase content of 7 to 12 wt. % or 8 to 12 wt. %.

A corundum crystal phase content in this range contributes to the strength of the sintered zirconia article and may further help to improve the ageing stability.

Further, the sintered zirconia article can typically be characterized by the following parameters alone or in combination:
a) zirconia crystal phase content of tetragonal phase: more than 85 wt. % or more than 90 wt. %;
b) zirconia crystal phase content of cubic phase: less than 2 wt. % or less than 1 wt. %;
c) zirconia crystal phase content of monoclinic phase: less than 2%; or less than 1 wt. %;
wt. % with respect to the weight of the sintered zirconia article.

Further, the sintered zirconia article can typically be characterized by the following parameters alone or in combination:
a) zirconia grain size: from 200 to 300 nm;
b) alumina grain size: from 200 to 300 nm
c) density: more than 98.5% with respect to theoretical density;
d) flexural strength: at least 2,000 MPa according to ISO 6872:2015;
e) fracture toughness: at least 7 MPa*m$^{0.5}$ according to ISO 6872:2015
f) density: more than 98.5% with respect to theoretical density;
g) translucency: less than 20% determined on a polished sample having a thickness of 1 mm.

According to certain embodiment, the combination of the following properties can be advantageous: d) and e); or d) and b); or d), a) and b).

In contrast to sintered zirconia articles described in the prior art, the translucency of the sintered zirconia article described in the present text is reduced. That is, the sintered zirconia article of described in the present text is more opaque.

The porous zirconia article and the sintered zirconia article described in the present text can have various shapes.

If the zirconia article is to be used in the dental or orthodontic field, the article may have the shape of a dental milling blank, a dental restoration, an orthodontic bracket, an implant, an abutment or part thereof.

Dental restorations include dental crowns, bridges, inlays, onlays, veneers, implants and parts thereof. The dental restorations also include so-called monolithic dental restorations.

The composition described in the present text can be used for the production of high strength zirconia articles.

The composition comprises the zirconium, yttrium and aluminum components, the amount of which with respect to the oxides is given as follows:
$ZrO_2$: 80 to 87 wt. %,
$Y_2O_3$: 3 to 5 wt. %,
$Al_2O_3$: 10 to 14 wt. %,
wt. % with respect to the weight of the composition.

Such a composition can be provided and used in different forms.

According to one embodiment, the composition is provided as a sol.

Such a sol typically comprises:
solvent,
$ZrO_2$ in the form of nano-sized yttria stabilized crystalline zirconia particles,
$Al_2O_3$ in the form of a colloidal suspension of alumina particles,
photoinitiator(s),
polymerizable monomer(s),
optionally inhibitor(s).

The nature and structure of the solvent is not particularly limited unless the desired result cannot be achieved.

In certain embodiments the solvent can be characterized by at least one or more, sometimes all of the following parameters:
Boiling point: above 70 or above 100 or above 120 or above 150° C.;
Molecular weight: from 25 to 300 or from 30 to 250 g/mol or from 40 to 200 g/mol or from 50 to 175 g/mol;
Viscosity: from 0.1 to 50 or from 0.2 to 10 or from 0.3 to 5 mPa*s (23° C.);
miscible with water;
soluble in supercritical carbon dioxide or liquid carbon dioxide.

Using a solvent with a boiling point above 100° C. or 150° C. can be beneficial for reducing the evaporation of the solvent during the process.

Using a solvent with a molecular weight and/or viscosity in the above range can be beneficial as it helps in adjusting the viscosity of the printing sol. The molecular weight size can also affect the diffusion constant and how easily the solvent can be removed.

Using a mixture of different solvents can be beneficial as it allows to adjust viscosity or post processing properties, e.g. removal of excess sol after printing.

The solvent should be able to dissolve the other components being present in the sol.

The solvent should also be easily removable during the further processing steps needed for the realization of a ceramic article.

Further, the solvent should not interfere with or negatively influence the polymerization of the radiation curable components being present in the sol.

In this respect, using solvents not bearing polymerizable moieties can be beneficial.

To enhance the dissolving capability or property of the solvent, the solvent typically bears one or more polar moieties, including ether, alcohol or carboxy moieties.

According to one embodiment, the solvent is often a glycol or polyglycol, mono-ether glycol or mono-ether polyglycol, di-ether glycol or di-ether polyglycol, ether ester glycol or ether ester polyglycol, carbonate, amide, or sulfoxide (e.g., dimethyl sulfoxide). The organic solvents usually have one or more polar groups. The organic solvent does not have a polymerizable group; that is, the organic solvent is free of a group that can undergo free radical polymerization. Further, no component of the solvent medium has a polymerizable group that can undergo free radical polymerization.

Suitable glycols or polyglycols, mono-ether glycols or mono-ether polyglycols, di-ether glycols or di-ether polyglycols, and ether ester glycols or ether ester polyglycols are often of the following Formula (I).

In Formula (I), each $R^1$ independently is hydrogen, alkyl, aryl, or acyl. Suitable alkyl groups often have 1 to 10 carbon atoms, 1 to 6 carbon atoms, or 1 to 4 carbon atoms. Suitable aryl groups often have 6 to 10 carbon atoms and are often phenyl or phenyl substituted with an alkyl group having 1 to 4 carbon atoms. Suitable acyl groups are often of formula —(CO)$R^a$ where $R^a$ is an alkyl having 1 to 10 carbon atoms, 1 to 6 carbon atoms, 1 to 4 carbon atoms, 2 carbon atoms, or 1 carbon atom. The acyl is often an acetyl group (—(CO)CH$_3$). In Formula (I), each $R^2$ is typically ethylene or propylene. The variable n is at least 1 and can be in a range of 1 to 10, 1 to 6, 1 to 4, or 1 to 3.

Glycols or polyglycols of Formula (I) have two R1 groups equal to hydrogen. Examples of glycols include, but are not limited to, ethylene glycol, propylene glycol, diethylene glycol, dipropylene glycol, triethylene glycol, and tripropylene glycol.

Mono-ether glycols or mono-ether polyglycols of Formula (I) have a first R1 group equal to hydrogen and a second R1 group equal to alkyl or aryl. Examples of mono-ether glycols or mono-ether polyglycols include, but are not limited to, ethylene glycol monohexyl ether, ethylene glycol monophenyl ether, propylene glycol monobutyl ether, diethylene glycol monomethyl ether, diethylene glycol monoethyl ether, diethylene glycol monopropyl ether, diethylene glycol monobutyl ether, diethylene glycol monohexyl ether, dipropylene glycol monomethyl ether, dipropylene glycol monoethyl ether, dipropylene glycol monopropyl ether, triethylene glycol monomethyl ether, triethylene glycol monoethyl ether, triethylene glycol monobutyl ether, tripropylene glycol monomethyl ether, and tripropylene glycol monobutyl ether.

Di-ether glycols or di-ether polyglycols of Formula (I) have two R1 group equal to alkyl or aryl. Examples of di-ether glycols or di-ether polyglycols include, but are not limited to, ethylene glycol dipropyl ether, ethylene glycol dibutyl ether, dipropylene glycol dibutyl ether, diethylene glycol dimethyl ether, diethylene glycol diethyl ether, triethylene glycol dimethyl ether, tetraethylene glycol dimethyl ether, and pentaethylene glycol dimethyl ether.

Ether ester glycols or ether ester polyglycols of Formula (I) have a first R1 group equal to an alkyl or aryl and a second R1 group equal to an acyl. Examples of ether ester glycols or ether ester polyglycols include, but are not limited to, ethylene glycol butyl ether acetate, diethylene glycol butyl ether acetate, and diethylene glycol ethyl ether acetate.

Other suitable organic solvents are carbonates of Formula (II).

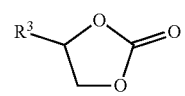

In Formula (II), R3 is hydrogen or an alkyl such as an alkyl having 1 to 4 carbon atoms, 1 to 3 carbon atoms, or 1 carbon atom. Examples include ethylene carbonate and propylene carbonate.

Yet other suitable organic solvents are amides of Formula (III).

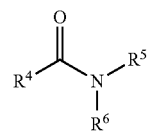

In Formula (III), group $R^4$ is hydrogen, alkyl, or combines with $R^5$ to form a five-membered ring including the carbonyl attached to $R^4$ and the nitrogen atom attached to $R^5$. Group $R^5$ is hydrogen, alkyl, or combines with $R^4$ to form a five-membered ring including the carbonyl attached to $R^4$ and the nitrogen atom attached to $R^5$. Group $R^6$ is hydrogen or alkyl. Suitable alkyl groups for $R^4$, $R^5$, and $R^6$ have 1 to 6 carbon atoms, 1 to 4 carbon atoms, 1 to 3 carbon atoms, or 1 carbon atom. Examples of amide organic solvents of Formula (III) include, but are not limited to, formamide, N,N-dimethylformamide, N,N-dimethylacetamide, N,N-diethylacetamide, N-methyl-2-pyrrolidone, and N-ethyl-2-pyrrolidone.

Specific examples of solvents which can be used include: mono alcohols (e.g. C2 to C8 alcohols, including primary, secondary and tertiary alcohols), poly alcohols (e.g. ethylene glycol, propylene glycol, glycerine, diethylene glycol ethyl ether (Carbitol™), 1-methoxy-2-propanol, N-methyl pyrrolidone, acetonitrile, chlorobenzene, 1,4-dioxane, ethyl acetate, methyl ethyl ketone, tetrahydrofuran, toluene, xylene and mixtures thereof.

The following solvents are sometimes preferred: ethanol, 1-methoxy-2-propanol, N-methyl pyrrolidone, diethylene glycol ethyl ether, and mixtures thereof. In some situations, suitable solvents may also include low boiling alcohols (below 100° C.; like methanol, ethanol, propanol) and mixtures thereof or preferably the same solvent(s) described above.

The solvent(s) is typically present in the following amounts:

Lower amount: at least 25 or at least 30 or at least 35 wt. %;

Upper amount: at most 70 or at most 65 or at most 60 wt. %;

Range: from 25 to 70 or from 30 to 65 or from 35 to 60 or from 35 to 55 or from 35 to 50 wt. %;
wt. % with respect to the weight of the sol.

The nature and structure of the nano-sized zirconia particles is not particularly limited, unless the desired result cannot be achieved.

In certain embodiments, the nano-sized zirconia particles(s) can be characterized by at least one or more, sometimes all of the following parameters or features:
primary particle size XRD (diameter): from 2 to 50 or from 2 to 20 nm or from 2 to 15 or from 4 to 15 nm;
being essentially spherical or cuboidal;
being non-associated;
being crystalline.

"Essentially spherical" means that the shape of the particles is close to a sphere. It does not contain sharp edges, which may result from a milling process.

According to one embodiment, the nano-sized zirconia particles are characterized as follows: $ZrO_2$ content: from 70 to 98.4 mol %; $HfO_2$ content: from 0.1 to 2.8 mol %; $Y_2O_3$ content: from 1.5 to 2.5 mol %.

The nano-sized zirconia particles can be obtained or are obtainable by a process comprising the steps of hydrothermal treatment of an aqueous metal salt solution or suspension (e.g. zirconium salt, yttrium salt). Such a process is described in WO 2013/055432 (3M), the content of which is herewith incorporated by reference.

The zirconia particles are contained in the sol in an amount of 2 to 25 vol. % or 4 to 18 vol. % or 5 to 16 vol. %.

With respect to wt. %, the sol typically contains 20 to 70 wt. % zirconia-based particles based on a total weight of the sol. The amount of zirconia-based particles can be at least 20 wt. %, at least 25 wt. %, at least 30 wt. %, at least 35 wt. %, or at least 40 wt. % and can be up to 70 wt. %, up to 60 wt. %, up to 50 wt. %, or up to 45 wt. %. In some embodiments, the amount of the zirconia-based particles are in a range of 20 to 70 wt. %, 25 to 60 wt. %, 30 to 55 wt. %, 30 to 50 wt. %, 40 to 50 wt. %, or 35 to 45 wt. % based on the total weight of the sol.

Alumina is typically provided as a colloidal suspension in a solvent.

The alumina particles typically have a mean particle size of 20 to 100 nm.

The solvent or liquid used for dispersing the alumina particles can be the same as used for producing the sol. Using water is sometimes preferred.

To obtain the desired alumina content, an alumina sol is typically added to the zirconia sol.

According to a further embodiment, the sol described in the present text comprises one or more inhibitor(s).

The nature and structure of the inhibitor(s) is not particularly limited, either, unless the desired result cannot be achieved.

An inhibitor may extend the shelf life of the printing sol, help prevent undesired side reactions, and adjust the polymerization process of the radiation curable component(s) present in the sol.

Adding one or more inhibitor(s) to the printing sol may further help to improving the accuracy or detail resolution of the surface of the ceramic article.

In particular it was found that adding inhibitor(s) to the printing sol described in the present text may help to enhance the resolution and accuracy of the SLA process by attenuating or avoiding unwanted scattering effects, as well as increase the shelf life of the printing sol.

The inhibitor(s) should be soluble in the solvent contained in the sol. Inhibitors which can be used often comprise a phenol moiety.

Specific examples of inhibitor(s) which can be used include: butylhydroxytoluol (Ionol), p-methoxyphenol (MOP), hydroquinone monomethylether (MEHQ), 2,6-di-tert-butyl-4-methyl-phenol (BHT), phenothiazine, 2,2,6,6-tetramethyl-piperidine-1-oxyl radical (TEMPO) and mixtures thereof.

If present, the inhibitor(s) is present in the following amounts:
Lower amount: at least 0.001 or at least 0.005 or at least 0.01 wt. %;
Upper amount: at most 0.02 or at most 0.05 or at most 0.5 wt. %;
Range: from 0.001 to 0.5 or from 0.005 to 0.15 wt. %;
wt. % with respect to the weight of the printing sol.

In order to make the sol light curable, the sol typically comprises one or more photoinitiator(s).

The nature and structure of the photoinitiator is not particularly limited, either, unless the desired result cannot be achieved.

In certain embodiments the photoinitiator(s) can be characterized by at least one or more, sometimes all of the following parameters:
soluble in the solvent contained in the sol;
radiation absorption: within a range from 200 to 500 or from 300 to 450 nm.

The photoinitiator should be able to start or initiate the curing or hardening reaction of the radiation curable component(s) being present in the sol.

The following classes of photoinitiator(s) can be used: a) two-component system where a radical is generated through abstraction of a hydrogen atom form a donor compound; b) one component system where two radicals are generated by cleavage.

Examples of photoinitiators according to type (a) typically contain a moiety selected from benzophenone, xanthone or quinone in combination with an aliphatic amine.

Examples of photoinitiators according to type (b) typically contain a moiety selected form benzoin ether, acetophenon, benzoyl oxime or acyl phosphine.

Exemplary UV initiators include 1-hydroxycyclohexyl benzophenone (previously available, for example, under the trade designation "IRGACURE™ 184" from Ciba Specialty Chemicals Corp., Tarrytown, N.Y.), 4-(2-hydroxyethoxy) phenyl-(2-hydroxy-2-propyl) ketone (available, for example, under the previous trade designation "IRGACURE™ 2529" from Ciba Specialty Chemicals Corp.), 2-hydroxy-2-methylpropiophenone (previously available, for example, under the trade designation "DAROCURE™ D111" from Ciba Specialty Chemicals Corp. and bis(2,4,6-trimethylbenzoyl)-phenylposphineoxide (previously available, for example, under the trade designation "IRGACURE™ 819" from Ciba Specialty Chemicals Corp.).

The photoinitiator(s) is typically present in the following amounts:
Lower amount: at least 0.01 or at least 0.1 or at least 0.5 wt. %;
Upper amount: at most 0.5 or at most 1.5 or at most 3 wt. %;
Range: from 0.01 to 3 or from 0.5 to 1.5 wt. %;
wt. % with respect to the weight of the printing sol.

The sol described in the present text comprises one or more radiation curable components being part of or forming an organic matrix.

The radiation curable components being present in the sol can be described as first, second, third, etc. monomer.

The nature and structure of the radiation curable component(s) is not particularly limited unless the desired result cannot be achieved.

Upon polymerization, the radiation curable components form a network with the homogeneously dispersed nano-sized zirconia particles.

The sol described in the present text may contain as a first monomer a polymerizable surface modification agent.

A surface modification agent may help to improve compatibility of the zirconia particles contained in the sol with an organic matrix material being present in the sol as well.

Surface modification agents may be represented by the formula A-B, where the A group is capable of attaching to the surface of a zirconia-based particle and the B group is radiation curable.

Group A can be attached to the surface of the zirconia-based particle by adsorption, formation of an ionic bond, formation of a covalent bond, or a combination thereof.

Examples for Group A include acidic moieties (like carboxylic acid groups, phosphoric acid groups, sulfonic acid groups and anions thereof) and silanes.

Group B comprises a radiation curable moiety.

Examples for Group B include vinyl, in particular acryl or methacryl moieties.

Suitable surface modifying agents comprise polymerizable carboxylic acids and/or anions thereof, polymerizable sulfonic acids and/or anions thereof, polymerizable phosphoric acids and/or anions thereof, and polymerizable silanes. Suitable surface modification agents are further described, for example, in WO 2009/085926 (Kolb et al.), the disclosure of which is incorporated herein by reference.

An example of a radically polymerizable surface modifier is a polymerizable surface modification agent comprising an acidic moiety or anion thereof, e.g. a carboxylic acid group.

Exemplary acidic radically polymerizable surface modifiers include acrylic acid, methacrylic acid, beta-carboxyethyl acrylate, and mono-2-(methacryloxyethyl)succinate.

Exemplary radically polymerizable surface modifiers can be reaction products of hydroxyl-containing polymerizable monomers with cyclic anhydrides such as succinic anhydride, maleic anhydride and phthalic anhydride. Exemplary polymerization hydroxyl-containing monomers include hydroxyethyl acrylate, hydroxyethyl methacrylate, hydroxypropyl acrylate, hydroxypropyl methacrylate, hydroxyl butyl acrylate, and hydroxybutyl methacrylate. Acryloxy and methacryloxy functional polyethylene oxide, and polypropylene oxide may also be used as the polymerizable hydroxyl-containing monomers.

An exemplary radically polymerizable surface modifier for imparting both polar character and reactivity to the zirconia-containing nanoparticles is mono(methacryloxypolyethyleneglycol) succinate.

Another example of a radically polymerizable surface modifier is a polymerizable silane.

Exemplary polymerizable silanes include methacryloxyalkyltrialkoxysilanes, or acryloxyalkyltrialkoxysilanes (e.g., 3-methacryloxypropyltrimethoxysilane, 3-acryloxypropyltrimethoxysilane, and 3-(methacryloxy)propyltriethoxysilane; as 3-(methacryloxy)propylmethyldimethoxysilane, and 3-(acryloxypropyl)methyldimethoxysilane); methacryloxyalkyldialkylalkoxysilanes or acyrloxyalkyldialkylalkoxysilanes (e.g., 3-(methacryloxy)propyldimethylethoxysilane); mercaptoalkyltrialkoxysilanes (e.g., 3-mercaptopropyltrimethoxysilane); aryltrialkoxy-silanes (e.g., styrylethyltrimethoxysilane); vinylsilanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, and vinyltris(2-methoxyethoxy)silane).

A surface modification agent can be added to the zirconia-based particles using conventional techniques. The surface modification agent can be added before or after any removal of at least a portion of the carboxylic acids and/or anions thereof from the zirconia-based sol. The surface modification agent can be added before or after removal of the water from the zirconia-based sol. The organic matrix can be added before or after surface modification or simultaneously with surface modification. Various methods of adding the surface modification agent are further described, for example, in WO 2009/085926 (Kolb et al.), the disclosure of which is incorporated herein by reference.

The surface modification reactions can occur at room temperature (e.g., 20° C. to 25° C.) or at an elevated temperature (e.g., up to 95° C.). When the surface modification agents are acids such as carboxylic acids, the zirconia-based particles typically can be surface-modified at room temperature. When the surface modification agents are silanes, the zirconia-based particles are typically surface modified at elevated temperatures.

The first monomer can function as a polymerizable surface modification agent. Multiple first monomers can be used. The first monomer can be the only kind of surface modification agent or can be combined with one or more other non-polymerizable surface modification agents. In some embodiments, the amount of the first monomer is at least 20 wt. % based on a total weight of polymerizable material. For example, the amount of the first monomer is often at least 25 wt. %, at least 30 wt. %, at least 35 wt. %, or at least 40 wt. %. The amount of the first monomer can be up to 100 wt. %, up to 90 wt. %, up to 80 wt. %, up to 70 wt. %, up to 60 wt. %, or up to 50 wt. %. Some printing sols contain 20 to 100 wt. %, 20 to 80 wt. %, 20 to 60 wt. %, 20 to 50 wt. %, or 30 to 50 wt. % of the first monomer based on a total weight of polymerizable material.

The first monomer (i.e. the polymerizable surface modification agent) can be the only monomer in the polymerizable material or it can be combined with one or more second monomers that are soluble in the solvent medium.

According to one embodiment, the sol described in the present text comprises one or more second monomers comprising at least one or two radiation curable moieties. Those second monomer(s) may act as crosslinker(s) during the gel-forming step.

Any suitable second monomer that does not have a surface modification group can be used. The second monomer does not have a group being capable of attaching to the surface of a zirconia-based particle.

A successful build typically requires a certain level of green body gel strength as well as shape resolution. A crosslinked approach often times allows for greater green body gel strength to be realized at a lower energy dose since the polymerization creates a stronger network. In some examples, higher energy doses have been applied to increase layer adhesion of non-crosslinked systems. While an article is successfully built, often times the higher energy impacts the resolution of the final article, causing overbuild to potentially occur, especially in the case of highly translucent materials where the cure depth can penetrate further into the material. An alternative solution involves the addition of an organic dye to decrease the cure depth, and therefore resolution realized with a higher energy dose, while still allowing for a greater degree of polymerization to occur due to a higher energy dose.

The presence of the monomer having a plurality of polymerizable groups tends to enhance the strength of the gel composition formed when the printing sol is polymerized. Such gel compositions can be easier to process without cracking. The amount of the monomer with a plurality of the polymerizable groups can be used to adjust the flexibility and the strength of the green body gel, and indirectly optimize the green body gel resolution and final article resolution.

In the case where the light source is applied from below, it was found that applying crosslink chemistry may help to increase the strength of the adhesion between layers so that when the build platform is raised after the cure step, the newly cured layer moves with the building shape, rather than being separated from the rest of the build and left behind on the transparent film, which would be considered a failed build.

A successful build could be defined as the scenario when the material adheres better to the previously cured layers than the build tray film to allow for a three-dimensional structure to be grown one layer at a time.

This performance could in theory be achieved by applying an increased energy dose (higher power, or longer light exposure) to provide a stronger adhesion up to a certain point characteristic of the bulk material. However, in a fairly transparent system where light absorbing additives are not present a higher energy exposure will eventually provide a depth of cure significantly greater than the 'slice thickness' creating an over-cured situation where the resolution of the part is significantly beyond that of the 'slice thickness'.

Adding a radiation curable component comprising at least two radiation curable moieties to the printing sol described in the present text facilitates the optimization of resolution as well as green body strength.

In the case of transforming the green body into a fully dense ceramic, increased green body gel strength aids in the robustness of the post-building procedures.

That is, the optional second monomer does not have a carboxylic acid group or a silyl group. The second monomers are often polar monomers (e.g., non-acidic polar monomers), monomers having a plurality of polymerizable groups, alkyl (meth)acrylates and mixtures thereof.

The overall composition of the polymerizable material is often selected so that the polymerized material is soluble in the solvent medium. Homogeneity of the organic phase is often preferable to avoid phase separation of the organic component in the gel composition. This tends to result in the formation of smaller and more homogeneous pores (pores with a narrower size distribution) in the subsequently formed dry gel. The dry gel may be a xerogel or aerogel. Further, the overall composition of the polymerizable material can be selected to adjust compatibility with the solvent medium and to adjust the strength, flexibility, and uniformity of the gel composition. Still further, the overall composition of the polymerizable material can be selected to adjust the burnout characteristics of the organic material prior to sintering.

In certain embodiments, the second monomer includes a monomer having a plurality of polymerizable groups. The number of polymerizable groups can be in a range of 2 to 6 or even higher. In many embodiments, the number of polymerizable groups is in a range of 2 to 5 or 2 to 4. The polymerizable groups are typically (meth)acryloyl groups.

Exemplary monomers with two (meth)acryloyl groups include 1,2-ethanediol diacrylate, 1,3-propanediol diacrylate, 1,9-nonanediol diacrylate, 1,12-dodecanediol diacrylate, 1,4-butanediol diacrylate, 1,6-hexanediol diacrylate, butylene glycol diacrylate, bisphenol A diacrylate, diethylene glycol diacrylate, triethylene glycol diacrylate, tetraethylene glycol diacrylate, tripropylene glycol diacrylate, polyethylene glycol diacrylate, polypropylene glycol diacrylate, polyethylene/polypropylene copolymer diacrylate, polybutadiene di(meth)acrylate, propoxylated glycerin tri(meth)acrylate, and neopentylglycol hydroxypivalate diacrylate modified caprolactone.

Exemplary monomers with three or four (meth)acryloyl groups include, but are not limited to, trimethylolpropane triacrylate (e.g., commercially available under the trade designation TMPTA-N from Cytec Industries, Inc. (Smyrna, Ga., USA) and under the trade designation SR-351 from Sartomer (Exton, Pa., USA)), pentaerythritol triacrylate (e.g., commercially available under the trade designation SR-444 from Sartomer), ethoxylated (3) trimethylolpropane triacrylate (e.g., commercially available under the trade designation SR-454 from Sartomer), ethoxylated (4) pentaerythritol tetraacrylate (e.g., commercially available under the trade designation SR-494 from Sartomer), tris(2-hydroxyethylisocyanurate) triacrylate (e.g., commercially available under the trade designation SR-368 from Sartomer), a mixture of pentaerythritol triacrylate and pentaerythritol tetraacrylate (e.g., commercially available from Cytec Industries, Inc., under the trade designation PETIA with an approximately 1:1 ratio of tetraacrylate to triacrylate and under the trade designation PETA-K with an approximately 3:1 ratio of tetraacrylate to triacrylate), pentaerythritol tetraacrylate (e.g., commercially available under the trade designation SR-295 from Sartomer), and di-trimethylolpropane tetraacrylate (e.g., commercially available under the trade designation SR-355 from Sartomer).

Exemplary monomers with five or six (meth)acryloyl groups include, but are not limited to, dipentaerythritol pentaacrylate (e.g., commercially available under the trade designation SR-399 from Sartomer) and a hexa-functional urethane acrylate (e.g., commercially available under the trade designation CN975 from Sartomer).

Some sol compositions contain 0 to 80 wt. % of a second monomer having a plurality of polymerizable groups based on a total weight of the polymerizable material. For example, the amount can be in a range of 10 to 80 wt. %, 20 to 80 wt. %, 30 to 80 wt. %, 40 to 80 wt. %, 10 to 70 wt. %, 10 to 50 wt. %, 10 to 40 wt. %, or 10 to 30 wt. %.

In some embodiments, the optional second monomer is a polar monomer.

As used herein, the term "polar monomer" refers to a monomer having a free radical polymerizable group and a polar group. The polar group is typically non-acidic and often contains a hydroxyl group, a primary amido group, a secondary amido group, a tertiary amido group, an amino group, or an ether group (i.e., a group containing at least one alkylene-oxy-alkylene group of formula —R—O—R— where each R is an alkylene having 1 to 4 carbon atoms).

Suitable optional polar monomers having a hydroxyl group include, but are not limited to, hydroxyalkyl (meth)acrylates (e.g., 2-hydroxyethyl (meth)acrylate, 2-hydroxypropyl (meth)acrylate, 3-hydroxypropyl (meth)acrylate, and 4-hydroxybutyl (meth)acrylate), and hydroxyalkyl (meth)acrylamides (e.g., 2-hydroxyethyl (meth)acrylamide or 3-hydroxypropyl (meth)acrylamide), ethoxylated hydroxyethyl (meth)acrylate (e.g., monomers commercially available from Sartomer (Exton, Pa., USA) under the trade designation CD570, CD571, and CD572), and aryloxy substituted hydroxyalkyl (meth)acrylates (e.g., 2-hydroxy-2-phenoxypropyl (meth)acrylate).

Exemplary polar monomers with a primary amido group include (meth)acrylamide. Exemplary polar monomers with secondary amido groups include, but are not limited to, N-alkyl (meth)acrylamides such as N-methyl (meth)acrylamide, N-ethyl (meth)acrylamide, N-isopropyl (meth)acrylamide, N-tert-octyl (meth)acrylamide, and N-octyl (meth)acrylamide. Exemplary polar monomers with a tertiary amido group include, but are not limited to, N-vinyl caprolactam, N-vinyl-2-pyrrolidone, (meth)acryloyl morpholine, and N,N-dialkyl (meth)acrylamides such as N,N-dimethyl (meth)acrylamide, N,N-diethyl (meth)acrylamide, N,N-dipropyl (meth)acrylamide, and N,N-dibutyl (meth)acrylamide.

Polar monomers with an amino group include various N,N-dialkylaminoalkyl (meth)acrylates and N,N-dialkylaminoalkyl (meth)acrylamides. Examples include, but are not limited to, N,N-dimethyl aminoethyl (meth)acrylate, N,N-dimethylaminoethyl (meth)acrylamide, N,N-dimethylaminopropyl (meth)acrylate, N,N-dimethylaminopropyl (meth)acrylamide, N,N-diethylaminoethyl (meth)acrylate, N,N-diethylaminoethyl (meth)acrylamide, N,N-diethylaminopropyl (meth)acrylate, and N,N-diethylaminopropyl (meth)acrylamide.

Exemplary polar monomers with an ether group include, but are not limited to, alkoxylated alkyl (meth)acrylates such as ethoxyethoxyethyl (meth)acrylate, 2-methoxyethyl (meth)acrylate, and 2-ethoxyethyl (meth)acrylate; and poly(alkylene oxide) (meth)acrylates such as poly(ethylene oxide) (meth)acrylates, and poly(propylene oxide) (meth)acrylates. The poly(alkylene oxide) acrylates are often referred to as poly(alkylene glycol) (meth)acrylates. These monomers can have any suitable end group such as a hydroxyl group or an alkoxy group. For example, when the end group is a methoxy group, the monomer can be referred to as methoxy poly(ethylene glycol) (meth)acrylate.

Suitable alkyl (meth)acrylates that can be used as a second monomer can have an alkyl group with a linear, branched, or cyclic structure. Examples of suitable alkyl (meth)acrylates include, but are not limited to, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, 2-methylbutyl (meth)acrylate, n-hexyl (meth)acrylate, cyclohexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth)acrylate, 3,3,5-trimethylcyclohexyl (meth)acrylate, n-decyl (meth)acrylate, isodecyl (meth)acrylate, isobornyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth) acrylate, and heptadecanyl (meth)acrylate.

The amount of a second monomer that is a polar monomer and/or an alkyl (meth)acrylate monomer is often in a range of 0 to 40 wt. %, 0 to 35 wt. %, 0 to 30 wt. %, 5 to 40 wt. %, or 10 to 40 wt. % based on a total weight of the polymerizable material.

The total amount of polymerizable material is often at least 2 wt. %, at least 3 wt. %, at least 5 wt. %, or at least 10 wt. % based on the total weight of the printing sol. The amount of polymerizable material can be up to 30 wt. %, up to 25 wt. %, up to 20 wt. %, or up to 15 wt. % based on the total weight of the printing sol. For example, the amount of polymerizable material can be in a range of 2-30 wt. %, 3-20 wt. %, or 5-15 wt. % based on the total weight of the printing sol.

Overall, the polymerizable material typically contains 20 to 100 wt. % first monomer and 0 to 80 wt. % second monomer based on a total weight of polymerizable material. For example, polymerizable material includes 30 to 100 wt. % first monomer and 0 to 70 wt. % second monomer, 30 to 90 wt. % first monomer and 10 to 70 wt. % second monomer, 30 to 80 wt. % first monomer and 20 to 70 wt. % second monomer, 30 to 70 wt. % first monomer and 30 to 70 wt. % second monomer, 40 to 90 wt. % first monomer and 10 to 60 wt. % second monomer, 40 to 80 wt. % first monomer and 20 to 60 wt. % second monomer, 50 to 90 wt. % first monomer and 10 to 50 wt. % second monomer, or 60 to 90 wt. % first monomer and 10 to 40 wt. % second monomer.

In some applications, it can be advantageous to minimize the weight ratio of polymerizable material to zirconia-based particles in the reaction mixture. This tends to reduce the amount of decomposition products of organic material that needs to be burned out prior to formation of the sintered article. The weight ratio of polymerizable material to zirconia-based particles is often at least 0.05, at least 0.08, at least 0.09, at least 0.1, at least 0.11, or at least 0.12. The weight ratio of polymerizable material to zirconia-based particles can be up to 0.80, up to 0.6, up to 0.4, up to 0.3, up to 0.2, or up to 0.1. For example, the ratio can be in a range of 0.05 to 0.8, 0.05 to 0.6, 0.05 to 0.4, 0.05 to 0.2, 0.05 to 0.1, 0.1 to 0.8, 0.1 to 0.4, or 0.1 to 0.3.

In certain embodiments, the second monomer(s) can be characterized the following parameters alone or in combination:

soluble in the solvent contained in the sol;

bearing at least one or two or three radiation curable moieties;

bearing radiation curable moieties selected from vinyl, acryl or methacryl moieties;

molecular weight from 70 to 5,000 or from 70 to 1,000 g/mol or from 100 to 500 g/mol.

Using radiation curable component(s) as described above having a molecular weight in the above range facilitates the provision of a sol having the desired viscosity. Lower molecular weight components are typically also better soluble than high molecular weight components.

If present, the second monomer is typically present in the following amounts:

Lower amount: at least 0.5 or at least 1 or at least 3 wt. %;

Upper amount: at most 5 or at most 10 or at most 24 wt. %;

Range: from 0.5 to 24 or from 3 to 10 wt. %;

wt. % with respect to the weight of the sol.

In addition to the radically polymerizable surface modifiers described above, the sol described in the present text may also comprise a surface modification agent without a polymerizable group that can undergo free radical polymerization reactions.

Such an optional surface modification agent is usually a carboxylic acid or salt thereof, sulfonic acid or salt thereof, phosphoric acid or salt thereof, phosphonic acid or salt thereof, or silane that can attach to a surface of the zirconia-based particles. In many embodiments, the optional surface modification agents are carboxylic acids that do not contain a polymerizable group that can undergo a free radical polymerization reaction.

In some embodiments, the optional non-polymerizable surface modification agent is a carboxylic acid and/or anion thereof and has a compatibility group that imparts a polar character to the zirconia-based nanoparticles. For example, the surface modification agent can be a carboxylic acid and/or anion thereof having an alkylene oxide or polyalkylene oxide group. In some embodiments, the carboxylic acid surface modification agent is of the formula (IV).

In this formula, Q is a divalent organic linking group, z is an integer in the range of 1 to 10, and y is an integer in the range of 1 to 4. The group Q includes at least one alkylene group or arylene group and can further include one or more oxy, thio, carbonyloxy, carbonylimino groups. Representative examples of this formula include, but are not limited to, 2-[2-(2-methoxyethoxy)ethoxy]acetic acid (MEEAA) and 2-(2-methoxyethoxy)acetic acid (MEAA). Still other representative carboxylic acids are the reaction product of an aliphatic anhydride and a polyalkylene oxide mono-ether such as succinic acid mono-[2-(2-methoxy-ethoxy)-ethyl] ester, and glutaric acid mono-[2-(2-methoxy-ethoxy)-ethyl] ester.

In other embodiments, the optional non-polymerizable surface modification agent is a carboxylic acid and/or anion thereof and the compatibility group can impart a non-polar character to the zirconia-containing nanoparticles. For example, the surface modification agent can be a carboxylic acid of formula $R^c$—COOH or a salt thereof where $R^c$ is an alkyl group having at least 5 carbon atoms, at least 6 carbon atoms, at least 8 carbon atoms, or at least 10 carbon atoms. $R^c$ often has up to 20 carbon atoms, up to 18 carbon atoms, or up to 12 carbon atoms. Representative examples include octanoic acid, lauric acid, dodecanoic acid, stearic acid, and combinations thereof.

In addition to modifying the surface of the zirconia-based particles to minimize the likelihood of agglomeration and/or aggregation when the sol is concentrated, the optional non-polymerizable surface modification agent can be used to adjust the viscosity of the sol.

Any suitable amount of the optional non-polymerizable surface modification agent can be used.

If present, the optional non-polymerizable surface modification agent usually is added in an amount equal to at least 0.5 wt. % based on the weight of the zirconia-based particles. For example, the amount can be equal to at least 1 wt. %, at least 2 wt. %, at least 3 wt. %, at least 4 wt. %, or at least 5 wt. % and can be up to 15 wt. % or more, up to 12 wt. %, up to 10 wt. %, up to 8 wt. %, or up to 6 wt. %. The amount of the optional non-polymerizable surface modification agent is typically in a range of 0 to 15 wt. %, 0.5 to 15 wt. %, 0.5 to 10 wt. %, 1 to 10 wt. %, or 3 to 10 wt. % based on the weight of the zirconia-based particles.

Stated differently, the amount of the optional non-polymerizable surface modification agent is often in a range of 0 to 10 wt. % based on a total weight of the sol. The amount is often at least 0.5 wt. %, at least 1 wt. %, at least 2 wt. %, or at least 3 wt. % and can be up to 10 wt. %, up to 8 wt. %, up to 6 wt. %, or up to 5 wt. % based on the total weight of the printing sol.

According to one embodiment, the sol described in the present text to be used as construction material in an additive manufacturing process is characterized as follows:
  Solvent content: from 25 to 70 or from 40 to 65 wt. %, the solvent having preferably a boiling point above 70° C. and being preferably selected from alcohols and glycol ethers;
  Nano-sized crystalline yttria stabilized zirconia particles content: from 20 to 70 or from 30 to 50 wt. %;
  Nano-sized alumina particle content: from 2 to 10 or from 3 to 7 wt. %,
  Polymerizable material content: from 2 to 30 wt. %, or from 3 to 20 wt. % or from 5 to 15 wt. %, the polymerizable material comprising a first monomer having at least one radiation curable moiety and an acidic or silyl moiety;
  Photoinitiator content: from 0.01 to 3 or from 0.5 to 1.5 wt. %;
  Inhibitor content: from 0 to 0.5 or from 0.001 to 0.15 wt. %;
wt. % with respect to the weight of the printing sol.

The sol can typically be characterized by the following features alone or in combination:
  a) showing a transmission of at least 5% at 420 nm determined for a path length of 1 cm;
  b) substantially free of associated nano-sized zirconia particles;
  c) being acidic, i.e. having a pH in the range of 1 to 6 or 2 to 5 or 2 to 4 if brought in contact with a wet pH sensitive paper;
  d) viscosity: less than 500 or less than 300 or less 200 or less than 180 or less than 150 or less than 100 or less than 50 or less than 20 mPa*s at 23° C.

The sol can be produced by a process as described e.g. in WO 2013/055432 A1 (3M) relating to aerogels, calcined articles and crystalline articles comprising zirconia and methods of making the same.

U.S. Pat. No. 7,429,422 (Davidson et al.) also describes methods of making zirconia-based sols, which can be used.

Further sols which can be used are described in U.S. application No. 62/127,569 (3M) filed Mar. 3, 2015. The above references are herewith incorporated by reference.

The invention also relates to processes for producing a porous zirconia article.

The porous zirconia article can be produced by applying a sol casting process or an additive manufacturing process.

According to another embodiment, a process for producing a porous zirconia article as described in the present text comprises the steps of:
  providing a sol as described in the present text,
  processing the sol as construction material in an additive manufacturing process to obtain a 3-dim article being in a gel state,
  transferring the 3-dim article being in a gel state to a 3-dim article being in a dry state, preferably by applying a supercritical drying step to the 3-dim article being in a gel state to form an aerogel,
  applying a heat treatment or pre-sintering step to obtain the porous zirconia article.

According to one embodiment, in the process of producing a ceramic article as described in the present text, the processing step comprises the steps of
  forming a layer or part thereof from the construction material on a surface,
  at least partially radiation curing the layer or part thereof,
  forming an additional layer or part thereof in contact with the radiation cured or partially cured surface of the previous layer,
  repeating the previous steps until a 3-dim article is obtained.

Further details of such a processing step are described in U.S. Pat. No. 4,575,330 (Hull), U.S. Pat. No. 6,283,997 (Garg et al.) or U.S. Pat. No. 8,003,040 B2 (El-Siblani). The content of these documents is herewith incorporated by reference.

The processing of the sol can be done by using or applying at least one or more of the following parameters:

Slice thickness of printing sol exposed to radiation: 0.001 to 0.500 mm or 0.01 to 0.4 mm;

Energy dose per layer in the range of 5 mJ/cm$^2$ to 100 mJ/cm$^2$ or 8 mJ/cm$^2$ to 50 mJ/cm$^2$.

According to a further embodiment, a process for producing a porous zirconia article as described in the present text comprises the steps of:
  providing a sol as described in the present text,
  casting the sol into a mold,
  curing the sol to obtain a 3-dim article being in a gel state,
  transferring the 3-dim article being in a gel state to a 3-dim article being in a dry state, preferably by applying a supercritical drying step to the 3-dim article being in a gel state to form an aerogel,
  optionally conducting a de-bindering process to remove organic material,
  applying a pre-sintering step to obtain the porous zirconia article.

Curing of the sol is typically done by applying heat or radiation or a combination of both, preferably by radiation.

The transfer of the 3-dim article being in a gel state to a 3-dim article being in a dry state is typically done in the same way as described above with respect to the additive-manufacturing technique.

Before a pre-sintering step is done, a further heating step is conducted to remove organic material present in the 3-dim article. Removing organic material before sintering reduces the risk of cracks during sintering.

Such a heating step is sometimes also referred to as de-bindering or calcining step.

Such a heating step is typically conducted at a temperature below 800° C. or below 700 or below 600° C. A typical temperature range is from 400 to 800° C. or from 500 to 700° C.

The heating step is typically conducted for a time needed to combust the organic components in the 3-dim article.

A typical time frame is from 5 to 100 h or from 10 to 50 h.

The heating is typically conducted at ambient conditions (i.e. ambient air, ambient pressure).

The pre-sintering step is typically done under the following conditions:
  temperature: from 800 to 1100° C. or from 950 to 1090° C. or from 975 to 1080° C.;
  atmosphere: air or inert gas (e.g. nitrogen, argon);
  duration: until a density of 40 to 60% of the final density of the material has been reached.

More precisely, the dried gel body is typically placed on zirconia beads, which may be located in an alumina crucible. If desired, the crucible is covered with e.g. alumina fiberboard and is fired in air using one or more firing steps.

Suitable firing conditions for the pre-sintering step are as follows:
  Heat from 20° C. to 200° C. at 18° C./hour rate,
  Heat from 200° C. to 250° C. at 1° C./hour rate,
  Heat from 250° C. to 400° C. at 6° C./hour rate,
  Heat from 400° C. to 1020° C. at 60° C./hour rate,
  Cool from 1020° C. to 20° C. at 120° C./hour rate.

The invention also relates to processes of producing a sintered zirconia article.

According to one embodiment, the sintered zirconia article is produced by a process comprising the steps of:
  providing the porous zirconia article as described in the present text, or the porous zirconia article obtainable by one of the processes described in the present text,
  applying a sintering step to obtain the sintered zirconia article.

The sintering step is typically done under the following conditions:
  temperature: from 1150 to 1500° C. or from 1200 to 1400° C. or from 1250 to 1350° C. or from 1200 to 1400° or from above 1300 to 1400° C. or above 1320° C. to 1400° C. or above 1340° C. or above 1350° C.;
  atmosphere: air or inert gas (e.g. nitrogen, argon);
  pressure: ambient pressure;
  duration: until a density of about 98.5 to about 100% of the final density of the material has been reached.

At the end, a densely sintered zirconia material is obtained, having a density close to the theoretically possible maximum density.

The process for producing a sintered zirconia article does not require a hot isostatic pressing step (HIP).

Such a HIP process is typically required, if a zirconia article with a flexural strength above 2,000 MPa is desired.

More precisely, suitable sintering conditions are described as follows:

The pre-sintered body is placed in an oven, e.g. on a bed of zirconia beads located in an alumina crucible. If desired, the crucible is covered with an alumina fiberboard and the sample is sintered in air according to the following schedule:
  Heat from 20° C. to 1020° C. at 600° C./hour rate,
  Heat from 1020° C. to 1450° C. at 120° C./hour rate,
  Hold at 1450° C. for 2 hours,
  Cool down from 1450° C. to 20° C. at 600° C./hour rate.

According to one embodiment, the sintered zirconia article described in the present text can be obtained as follows:
  provide a zirconia sol as described in the present text, the zirconia sol having a zirconia content in the range of 50 to 70 wt. %,
  add an yttrium component as described in the present text to obtain a sol having an yttrium content in an amount below 3 wt. %,
  add a colloidal suspension of alumina as described in the present text to obtain a sol having an alumina content in the range of 10 to 30 wt. %,
  add photoinitiators and polymerizable component(s) as described in the present text,
  cast the sol into a mould and light cure the sol or process the sol by an additive manufacturing process as described in the present text,
  remove the 3-dim article from the mould or remove the 3-dim article from the additive manufacturing device,
  optionally conduct a solvent exchange process, e.g. by storing the sample in ethanol,
  optionally conduct a supercritical extraction step e.g. by using liquid carbon dioxide,
  conduct a heating step to remove the organic binder, e.g. by apply temperature up to 800° C.,
  conduct a pre-sintering step as described in the present text, e.g. apply temperature up to 1080° C.,
  conduct a sintering step as described in the present text, e.g. apply temperature above 1150° C. or 1250° C. or 1350° C.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope thereof. The following examples are given to illustrate, but not limit, the scope of the invention.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Materials

| Material or abbreviation | Description |
|---|---|
| MEEAA | 2-(2-(2-Methoxyethoxy) Ethoxy) Acetic Acid |
| Zirconium acetate | An aqueous solution of zirconium acetate containing nominally 16.3 weight percent zirconium obtained from Magnesium Elektron, Inc., Flemington, NJ, USA. The aqueous solution was exposed to an ion exchange resin (obtained under the trade designation "AMBERLYTE IR 120" from Rohm and Haas Company, Philadelphia, PA, USA) before use (oxide content 21.85 wt. %). |
| Yttrium acetate | Yttrium (III) acetate tetrahydrate (oxide content 33.4 wt. %). |
| Aluminum Oxide | Aluminum Oxide in $H_2O$, colloidal dispersion (oxide content 20 wt. %) |
| DI water | De-ionized water. |
| HEMA | 2-Hydroxyethyl methacrylate |
| "Irgacure ™ 819" | UV/Visible photoinitiator from BASF Corporation Vandalia, IL, USA. |
| "SR454" | Ethoxylated trimethylolpropane triacrylate, obtained from Sartomer Company Inc., Exton, PA, USA. |
| DMF | N,N-Dimethylformamide |
| "SR506A" | Isobornyl acrylate obtained from Sartomer Company Inc., Exton, PA, USA. |
| "SR238B" | 1,6-Hexanediol diacrylate obtained from Sartomer Company Inc., Exton, PA, USA. |
| "SR295" | Pentaerythritol tetraacrylate obtained from Sartomer Company Inc., Exton, PA, USA. |
| "CN975" | Hexafunctional urethane acrylate obtained from Sartomer Company Inc., Exton, PA, USA. |
| HEAA | N-(2-Hydroxyethyl) acrylamide |
| HEAS | Mono-2-(Methacryloyloxy) ethyl succinate |
| B-CEA | Beta-carboxyethylacrylate |
| 4-Hydroxy-TEMPO | 4-Hydroxy-2,2,6,6-tetramethylpiperidin-1-oxyl |
| 3-(methacryloyl-oxy)-propyltri-methoxy-silane | 3-(methacryloyloxy)-propyltrimethoxysilane |
| Ammonium Hydroxide | Ammonium Hydroxide (assay 28-30 wt. % as $NH_3$) |
| CE1 | Commercially available $ZrO_2$ sold under the brand Lava ™ Plus by 3M (3Y-TZP) |
| CE3 | Commercially available $ZrO_2$ powder sold by Tosoh Corporation as TZ3YS20AB (batch#: SA23579B) |

Methods

Method for Determining Total Pore Volume, Average Connected Pore Diameter and BET Surface Area Total pore volume and average pore diameter were analyzed with the use of $N_2$ sorption Isotherms and BET surface area analysis. Samples of around 0.3-0.5 grams were cut if necessary from larger samples in order to be inserted in to the straight tubes. All samples were degassed for more than 1 day at 100° C. before analysis. The samples were then analyzed by adsorption and desorption of $N_2$ gas with a Quantachrome Autosorb IQ (Quantachrome Instruments, Florida, USA) in a 12 mm cell with no bulb and without a rod. Absorption data points are collected from 0.0003 to 0.995 P/PO and desorption points collected from 0.995 to 0.05 P/PO. The analysis has been duplicated (or triplicated if repeatability was not ideal), and the averaged results reported. The specific surface area S was calculated by the BET method (Details regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity (p/p0 closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume $V_{liq}$:

$$d = \frac{4V_{liq}}{S}.$$

Total pore volume and average pore diameter are reported as determined by Nonlocal Density Functional Theory method.

Method for Measuring Archimedes Density

The density of the sintered material was measured by the Archimedes technique. The measurements were made on a precision balance (identified as "AE 160" from Mettler Instrument Corp., Hightstown, N.J., USA) using a density determination kit (identified as "ME 33360" from Mettler Instrument Corp., Hightstown, N.J.). In this procedure, the sample was first weighed in air (A), then immersed in water (B) and weighed. The water was distilled and deionized. One drop of a wetting agent (obtained under trade designation "TERGITOL-TMN-6" from Dow Chemical Co., Danbury, Conn., USA) was added to 250 ml of water. The density was calculated using the formula $\rho=(A/(A-B))\,\rho 0$, where $\rho 0$ is the density of water. The relative density can be calculated by reference to the theoretical density ($\rho t$) of the material, $\rho rel=(\rho/\rho t)100$.

Method for Measuring Flexural Strength of Ceramic Article

The flexural strength was determined according to ISO 6872 (2015). The test piece is cutted from a presintered block and processed according to the invention to flex bars with approximate dimensions of 1.2 mm×4 mm×16 mm. All faces of the flex bar were polished down to a surface finish from 20 micron grade diamond suspension on a polishing textile (e.g. Leco Spectrum System 100 polishing machine), operating at 100 rpm. Each of the 4 edges along the length of the flex bar were chamfered, meaning to create a bevel on the edges of the specimens along, to a 45 degree angle. A 3-point beam bend test configuration with a span of 12.0 mm was employed. The crosshead test speed was 1 mm/min. An Instron 5566 test frame (Instron Corporation, Canton, Mass.) was utilized. A minimum of 10 samples were measured to determine the average strength.

Method for Measuring Translucency of Ceramic Article

The translucency of the ceramic articles was evaluated with the following procedure. The test piece is printed and processed as described in the present text in the shape of a disc with approximate dimensions of 1±0.03 mm thick×13 mm diameter or edge length. The parallel large faces of the disc were polished down to a surface finish from 9 micron grade diamond suspension on a polishing textile on a polishing machine (e.g. Leco Spectrum System 100), operating at 100 rpm. The polished sample was measured with a spectrophotometer (e.g. X-Rite Color i7, Grand Rapids, USA) in remission using the contrast ratio method. Translucency is determined according to Translucency=1−RB/RW where RB=reflectance through a ceramic disc on a black substrate and RW=reflectance through the same disc on a white substrate. Higher values of translucency are indicative of greater transmission of light, and less opacity. A minimum of 1 sample was measured to determine the average translucency.

Method for Crystalline Structure and Size (XRD Analysis)

Dried zirconia samples were ground by hand using an agate mortar and pestle. A liberal amount of the sample was applied by spatula to a glass microscope slide on which a section of double-sided adhesive tape had been adhered. The sample was pressed into the adhesive on the tape by forcing the sample against the adhesive with the spatula blade. Excess sample was removed by scraping the sample area with the edge of the spatula blade, leaving a thin layer of particles adhered to the adhesive. Loosely adhered materials remaining after the scraping were removed by forcefully tapping the microscope slide against a hard surface. In a similar manner, corundum (Linde 1.0 µm alumina polishing powder, Lot Number C062, Union Carbide, Indianapolis, Ind.) was prepared and used to calibrate the X-ray diffractometer for instrumental broadening.

X-ray diffraction scans were obtained using a Philips vertical diffractometer having a reflection geometry, copper Kα radiation, and a proportional detector registry of the scattered radiation. The diffractometer was fitted with variable incident beam slits, fixed diffracted beam slits, and a graphite diffracted beam monochromator. The survey scan was recorded from 25 to 55 degrees two theta (2θ) using a step size of 0.04 degrees and a dwell time of 8 seconds. X-ray generator settings of 45 kV and 35 mA were used. Data for the corundum standard was collected on three separate areas of several individual corundum mounts. Likewise, data was collected on three separate areas of the thin layer sample mount.

The observed diffraction peaks were identified by comparison to reference diffraction patterns contained within the International Center for Diffraction Data (ICDD) powder diffraction database (sets 1-47, ICDD, Newton Square, Pa., USA). The diffraction peaks for the samples were attributed to either cubic/tetragonal (C/T) or monoclinic (M) forms of zirconia. For zirconia-based particles, the (111) peak for the cubic phase and (101) peak for the tetragonal phase could not be separated so these phases were reported together. The amounts of each zirconia form were evaluated on a relative basis, and the form of zirconia having the most intense diffraction peak was assigned the relative intensity value of 100. The strongest line of the remaining crystalline zirconia form was scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting the observed diffraction peaks. The following peak widths were evaluated depending on the zirconia phase found to be present:

Cubic/Tetragonal (C/T): (1 1 1)
Monoclinic (M): (−1 1 1), and (1 1 1)

A Pearson VII peak shape model with Kα1 and Kα2 wavelength components and linear background model were used for all measurements. Widths were calculated as the peak full width at half maximum (FWHM) having units of degrees. The profile fitting was accomplished by use of the capabilities of the JADE diffraction software suite. Sample peak widths were evaluated for the three separate data collections obtained for the same thin layer sample mount.

Sample peaks were corrected for instrumental broadening by interpolation of instrumental breadth values from corundum instrument calibration and corrected peak widths converted to units of radians. The Scherrer equation was used to calculate the primary crystal size.

$$\text{Crystallite Size}(D) = K\lambda/\beta(\cos\theta)$$

In the Scherrer equation, K is the form factor (here 0.9), $\lambda$, is the wavelength (1.540598 Å), $\beta$ is the calculated peak width after correction for instrumental broadening (in radians), and $\theta$ equals half the peak position (scattering angle). $\beta$ is equal to [calculated peak FWHM−instrumental breadth] (converted to radians) where FWHM is full width at half maximum. The cubic/tetragonal (C/T) mean crystallite size was measured as the average of three measurements using (1 1 1) peak. That is, $$C/T \text{ mean crystallite size} = [D(1\ 1\ 1)_{area\ 1} + D(1\ 1\ 1)_{area\ 2} + D(1\ 1\ 1)_{area\ 3}]/3.$$

The monoclinic (M) crystallite size was measured as the average of three measurements using the
(−1 1 1) peak and three measurements using the (1 1 1) peak.

$$M \text{ mean crystallite size} = [D(-1\ 1\ 1)\text{area } 1 + D(-1\ 1\ 1)\text{area } 2 + D(-1\ 1\ 1)\text{area } 3 + D(1\ 1\ 1)\text{area } 1 + D(1\ 1\ 1)\text{area } 2 + D(1\ 1\ 1)\text{area } 3]/6$$

The weighted average of the cubic/tetragonal (C/T) and monoclinic phases (M) were calculated.

$$\text{Weighted average} = [(\%\ C/T)(C/T\ \text{size}) + (\%\ M)(M\ \text{size})]/100$$

In this equation, % C/T equals the percent crystallinity contributed by the cubic and tetragonal crystallite content of the $ZrO_2$ particles; C/T size equals the size of the cubic and tetragonal crystallites; % M equals the percent crystallinity contributed by the monoclinic crystallite content of the $ZrO_2$ particles; and M size equals the size of the monoclinic crystallites.

Method for Photon Correlation Spectroscopy (PCS)

Particle size measurements were made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample was analyzed in a one-centimeter square polystyrene sample cuvette. The sample cuvette was filled with about 1 gram of deionized water, and then a few drops (about 0.1 gram) of the zirconia-based sol were added. The composition (e.g., sample) within each sample cuvette was mixed by drawing the composition into a clean pipette and discharging the composition back into the sample cuvette several times. The sample cuvette was then placed in the instrument and equilibrated at 25° C. The instrument parameters were set as follows: dispersant refractive index 1.330, dispersant viscosity 0.8872 MPa-second, material refractive index 2.10, and material absorption value 0.10 units. The automatic size-measurement procedure was then run. The instrument automatically adjusted the laser-beam position and attenuator setting to obtain the best measurement of particle size.

The light scattering particle-sizer illuminated the sample with a laser and analyzed the intensity fluctuations of the light scattered from the particles at an angle of 173 degrees. The method of Photon Correlation Spectroscopy (PCS) was used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

Method for Determining Dispersion Index (DI)

The dispersion index is equal to the volume-average size measured using Photon Correlation Spectroscopy divided by the weighted average crystallite size measured by XRD.

Method for Determining Polydispersity Index (PI)

The polydispersity index is a measure of the breadth of the particle size distribution and is calculated along with the Z-average size in the cumulants analysis of the intensity distribution using Photon Correlation Spectroscopy. For values of the polydispersity index of 0.1 and below, the breadth of the distribution is considered narrow. For values above 0.5, the breadth of the distribution is considered broad and it is unwise to rely on the Z-average size to fully characterize the particle size. Instead, one should characterize the particles using a distribution analysis such as the intensity or volume distribution. The calculations for the Z-average size and polydispersity index are defined in the ISO 13321:1996 E ("Particle size analysis—Photon correlation spectroscopy", International Organization for Standardization, Geneva, Switzerland).

Method for Determining pH-Value

If desired, the measurement of the pH-value can be achieved by means known by the person skilled in art. E.g. an instrument like Metrohm™ 826 can be used.

Method for Measuring Wt. % Solids

The wt. % solids can be determined by drying a sample weighing 3-6 grams at 120° C. for 30 min. The percent solids can be calculated from the weight of the wet sample (i.e., weight before drying, $weight_{wet}$) and the weight of the dry sample (i.e., weight after drying, $weight_{dry}$) using the following equation: wt-% solids=100 ($weight_{dry}$)/$weight_{wet}$.

Method for Measuring Oxide Content

The oxide content of a sol sample was determined by measuring the percent solids content as described in the "Method for Measuring Wt. % Solids" then measuring the oxide content of those solids as described in this section.

The oxide content of a solid was measured via thermal gravimetric analysis (obtained under the trade designation "TGA Q500" from TA Instruments, New Castle, Del., USA).

The solids (about 50 mg) were loaded into the TGA and the temperature was taken to 900° C. The oxide content of the solid was equal to the residual weight after heating to 900° C.

Method for Determining Vol. % Oxide

The vol. % oxide in a sol can be determined by first using a volumetric flask to measure the mass of a known volume of sol, which gives the sol density $\rho_s$ in grams/ml. Then, using the wt. % oxide (measured as described above in "Method for Measuring Oxide Content"), the vol. % oxide was calculated as: vol. % oxide=($\rho_s$*wt. % oxide)/(oxide density), where a value of 6.05 grams/ml was used for the oxide density.

Method for Determining Viscosity

The viscosity was measured using a Brookfield Cone and Plate Viscometer (Model Number DV II available from Brookfield Engineering Laboratories, Middleboro, Mass., USA). The measurements were obtained using spindle CPE-42. The instrument was calibrated with Brookfield Fluid I which gave a measured viscosity of 5.12 mPa*s (cp) at 192 1/sec (50 RPM). The compositions were placed in the measurement chamber. Measurements were made at 3-4 different RPM (revolutions per minute). The measured viscosity was not significantly affected by the shear rate. The shear rate was calculated as 3.84 multiplied by the RPM. The viscosity values reported are for the minimum shear rate where the torque was in range.

Methods for Determining Fracture Toughness

Fracture Toughness was measured by "Single Edge V-Notch Beam" method (SEVNB) according to ISO 6873:2008 (Dental ceramic materials).

Fracture Toughness was also measured by "Anstis Crack length Method" introducing cracks with a Vickers diamond pyramid (2 kgf load, 15 s dwell time) on final sintered material samples. Tested sample surface was polished with 9 μm diamond suspension and a polishing textile until no scratches are visible. The samples were heat treated at 1300° C. for 30 min prior to sample loading. Fracture toughness was calculated from the crack length c in meters diagonal length of indentation d in mm, Vickers Hardness H or HV1 in GPa, Youngs modulus E in GPa and the indentation Force F in N acc. following equations $$K_{Ic} = 0.016 \left(\frac{E}{H}\right)^{1/2} \times \frac{F}{c^{3/2}}$$

and $$HV1 = \frac{0.1891 \cdot F}{d^2}$$

Method for Determining Hydrothermal Stability

Crystal phase composition of finally sintered material samples were measured initially by XRD analysis and stored in water vapor at 134° C. and 2 bar pressure. Crystal phase composition was measured again after 5, 30 and 75 hour's storage time. The lower the amount of monoclinic crystal phase after different storage period the higher is the hydrothermal stability of the material. That means the material show a higher resistance to undesired crystal phase change from tetragonal to monoclinic phase under humidity and elevated temperature.

Method for Determining Grain Size

If desired, grain size can be measured according ISO13356:2008 by Line intercept distance method.

Method for Microstructure Observation:

Finally, sintered samples were ground and polished with 9 μm diamond suspension until no scratches were visible. Polished samples were thermally etched at 1350° C. for 30 min.

Microstructural images were taken using a Scanning electron microscope (SEM) LEO 1530VP device (LEO Company) with 10.000× magnification and a working distance of 3.8 mm.

Processing

Preparation of Basic Sol

The Sol had a composition of $ZrO_2$ (97.7 mol %)/$Y_2O_3$ (2.3 mol %) in terms of inorganic oxides.

A hydrothermal reactor was used for preparing the Sol. The hydrothermal reactor was prepared from 15 meters of stainless steel braided smooth tube hose (0.64 cm inside diameter, 0.17 cm thick wall; obtained under the trade designation "DuPont T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DuPont T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm immersed in an ice-water bath to cool the material and a backpressure regulator valve was used to maintain an exit pressure of 3.45 MPa.

A precursor solution was prepared by combining the zirconium acetate solution (2,000 grams) with DI water (1,871.6 grams). Yttrium acetate (104.2 grams) was added while mixing until fully dissolved.

The solids content of the resulting solution was measured gravimetrically (120° C./hour, forced air oven) to be 19.26 weight %. D.I. water (54.4 grams) was added to adjust the final concentration to 19 weight %. The resulting solution was pumped at a rate of 11.48 ml/minute through the hydrothermal reactor. The temperature was 214° C. and the average residence time was 42 minutes. A clear and stable zirconia sol was obtained.

Table 1, below, summarizes the PCS data such as Z-average size (nm), polydispersity index (PI) and light transmission (% T) data for the basic Sol (at 1 weight % and 10 weight %) at 600 nm and 420 nm.

TABLE 1

| Z-Average Size (nm) | PI | Volume Average Size (nm) | % T @ 1% and 600 nm | % T @ 1% and 420 nm | % T @ 10% and 600 nm | % T @ 10% and 420 nm |
|---|---|---|---|---|---|---|
| 16.52 | 0.295 | 6.40 | 96.28 | 83.26 | 76.26 | 29.25 |

Table 2, below, summarizes the crystallite size and dispersion index (DI) data for the basic Sol determined from XRD analysis and photon correlation spectroscopy as described above.

TABLE 2

| M Intensity | M size (nm) | C/T intensity | C/T size (nm) | Volume Average (nm) | DI |
|---|---|---|---|---|---|
| 13 | 4.5 | 100 | 8.5 | 8.5 | 0.75 |

The basic Sol was further processed to increase concentration, remove acetic acid or incorporate ethanol. A combination of one or more of ultrafiltration, dia-filtration and distillation were used.

The dia-filtration and ultra-filtration were performed using a membrane cartridge (obtained under the trade designation "M21S-100-01P" from Spectrum Laboratories Inc., Rancho Dominguez, Calif.).

Distillation was performed using rotary evaporation.

Ethanol, acrylic acid, HEA and Irgacure™ 819 were added to the basic Sol and mixed until fully dissolved.

This basic Sol was used to generate 3 versions with different alumina content (Ex1, Ex2, EX3) and a reference without any alumina addition (CE2).

Alumina was added to the basic Sol in form of a water based colloidal suspension with 20 wt. % alumina content (Alfa Aesar; Aluminum Oxide, 20 wt. % in $H_2O$; colloidal dispersion, 50 nm) under mixing for about 30 min.

The basic Sol compositions are shown in Table 3.

Cast and curable ready Sol compositions are shown in Table 3.

TABLE 3

| Component in wt. % | CE2 | Ex1 | Ex2 | Ex3 |
|---|---|---|---|---|
| Sol | 82.34 | 73.97 | 73.97 | 73.97 |
| Ethanol | 10.23 | 9.19 | 9.19 | 9.19 |
| Acrylic acid | 4.85 | 4.35 | 4.35 | 4.35 |
| HEAA | 2.49 | 2.24 | 2.24 | 2.24 |
| Irgacure 819 | 0.09 | 0.08 | 0.08 | 0.08 |
| Aluminum oxide colloidal dispersion | 0.00 | 10.16 | 14.23 | 20.33 |

The compositions of CE1 and CE3 were processed using the following parameters:

axial pressing with 40 bar (4 MPa), iso-static pressing with 1980 bar (198 MPa), pre-sintering at 960° C. for 2 h.

Final compositions and characteristics of porous zirconia articles are shown in Tab. 4.

TABLE 4

Ex1* and Ex2* are reference examples.

| Properties | | CE1 | CE2 | CE3 | Ex1* | Ex2* | Ex3 |
|---|---|---|---|---|---|---|---|
| Chemical Composition by XRF [wt. %] | $ZrO_2$ | 92.2 | 94.5 | 73.6 | 88.3 | 86.5 | 83.4 |
| | $Y_2O_3$ | 5.7 | 3.7 | 4.4 | 3.4 | 3.4 | 3.2 |
| | $Al_2O_3$ | 0.1 | 0.0 | 20.4 | 6.5 | 8.3 | 11.6 |
| BET Surface [$m^2/g$] | | 5.7 | 12 | 4.9 | 11.3 | 12.2 | 12.1 |

The pre-sintered article of CE1 was further processed as follows:

sintering at 1450° C. for 2 hours.

The pre-sintered article of CE3 was further processed as follows:

sintering at 1400° C. for 2 hours, hot-isostatic pressing at 1500° C. with 152 MPa (1520 bar) under argon.

Final compositions and characteristics of fully processed and sintered materials are shown in Table 5.

TABLE 5

Ex1* and Ex2* are reference examples

| Properties | | CE1 | CE2 | CE3 | Ex1* | Ex2* | Ex3 |
|---|---|---|---|---|---|---|---|
| Chemical Composition by XRF [wt. %] | $ZrO_2$ | 92.2 | 94.5 | 73.6 | 88.3 | 86.5 | 83.4 |
| | $Y_2O_3$ | 5.7 | 3.7 | 4.4 | 3.4 | 3.4 | 3.2 |
| | $Al_2O_3$ | 0.1 | 0.0 | 20.4 | 6.5 | 8.3 | 11.6 |
| Crystal Phase Composition by XRD [wt. %] | Tetragonal | 80 | 100 | 64.5 | 95 | 93 | 91 |
| | Cubic | 20 | 0 | 13 | 0 | 0 | 0 |
| | Monoclinic | 0 | 0 | 0 | 0 | 0 | 0 |
| | Corundum | 0 | 0 | 22.5 | 5 | 7 | 9 |
| Grain size [µm] | $ZrO_2$ | 0.25 | 0.24 | 0.34 | 0.3 | 0.25 | 0.26 |
| | $Al_2O_3$ | — | — | 0.41 | 0.3 | 0.21 | 0.24 |

Preparation of Casted Mill Blanks, Screw and Bridge Geometries

The Sol/Alumina mixtures were cast pressure less into polycarbonate molds for mill blank format (CE2, Ex1, Ex2 and Ex3) or into negative molds made from agarose and water for screw (Ex2) and bridge geometries (Ex2).

The Sol filled molds were light cured for 4 minutes with Deloloux™ 450 lamps until the Sol has transformed to a Gel.

After demolding, the gel geometries were stored in ethanol for 4 days, changing the ethanol bath every 24 hours.

Preparation of 3D-Printed Samples by Stereolithography (SLA) Process

A Freeform Picoplus39 digital light projection printer from Asiga (Anaheim Hills, Calif.) was used to process the Sol of Ex2, into a 3-dim green body gel, which is then further processed into a highly dense ceramic article.

An STL file of test shape was loaded into the Asiga composer software. Next the parts were digitally placed on the build platform and selected process parameters were inputted. The 3-dim file was sliced with the included Asiga Composer software and digitally sent to the Freeform Picoplus39 printer.

The Freeform Picoplus39 printer operates in such a way that the build platform is lowered into the build tray previously filled with filtered printing sol to a programmed z-position. The digital light projector illuminates select pixels to selectively solidify a pattern of the of uncured sol layers. After the energy dose of light has been delivered, the build platform will move to the next z-position until the geometry was fully printed.

The Ex2 sol was printed at room temperature with parameter settings shown in Table 6.

TABLE 6

| | |
|---|---|
| Slice Thickness | 0.05 mm |
| Burn in Layers | 1 |
| Burn in Exposure time | 3 s |
| Separation distance | 5 mm |
| Separation velocity | 1 mm/s |
| Approach velocity | 5 mm/s |
| Slide Velocity | 10 mm/s |
| Slides/layer | 1 |

After the formation of the desired 3-dim green body gel, the build platform was removed from the printer and the green body gels were exposed to excess solvent to remove any uncured printing sol from the surface of the part.

The green body gels were then removed from the build platform with a scraping or cutting tool. The green body gels were removed shortly after the printing process finished and then stored in a sealed container to minimize the potential for solvent evaporation.

After demolding the Gel geometries were stored in ethanol for 4 days, changing the ethanol bath every 24 hours.

Super Critical Extraction of Gels

The supercritical extraction of the casted and light cured or 3D printed geometries was performed using a 10-L laboratory-scale supercritical fluid extractor unit designed by and obtained from Thar Process, Inc., Pittsburgh, Pa., USA. Sufficient ethanol was added to the 10-L extractor vessel to cover the gels (about 3500-6500 ml). The wet zirconia-based gels were loaded into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (set point: −8.0° C.) through a heat exchanger to heat the $CO_2$ to 60° C. and into the 10-L extractor vessel until an internal pressure of 13.3 MPa was reached. At these conditions, carbon dioxide is supercritical. Once the extractor operating conditions of 13.3 MPa and 60° C. were met, a needle valve regulated the pressure inside the extractor vessel by opening and closing to allow the extractor effluent to pass through a porous 316L stainless steel frit (obtained from Mott Corporation, New Britain, Conn., USA as Model #1100S-5.480 DIA-.062-10-A), then through a heat exchanger to cool the effluent to 30° C., and finally into a 5-L cyclone separator vessel that was maintained at room temperature and a pressure less than 5.5 MPa, where the extracted ethanol and gas-phase $CO_2$ were separated and collected throughout the extraction cycle for recycling and reuse. Supercritical carbon dioxide ($scCO_2$) was pumped continuously through the 10-L extractor vessel for 7 hours from the time the operating conditions were achieved. After the 7-hour extraction cycle, the extractor vessel was slowly vented into the cyclone separator over 16 hours from 13.3 MPa to atmospheric pressure at 60° C. before the lid was opened and the dried aerogels were removed.

De-Bindering and Pre-Sintering

The dried gel body was placed on a bed of zirconia beads in an alumina crucible.

The crucible was covered with alumina fiberboard and was fired in air according to the following schedule:

1—Heat from 20° C. to 190° C. at 18° C./hour rate,
2—Heat from 190° C. to 250° C. at 1° C./hour rate,
3—Heat from 250° C. to 400° C. at 6° C./hour rate,
4—Heat from 400° C. to 1020° C. at 60° C./hour rate,
5—Cool from 1020° C. to 20° C. at 120° C./hour rate.

Sintering

The pre-sintered bodies were placed on a bed of zirconia beads in an alumina crucible. The crucible was covered with alumina fiberboard and the sample was then sintered in air according to the following schedule:

1—Heat from 20° C. to 1020° C. at 600° C./hour rate,
2—Heat from 1020° C. to 1450° C. at 120° C./hour rate,
3—Hold at 1450° C. for 2 hours,
4—Cool down from 1450° C. to 20° C. at 600° C./hour rate.

Results

TABLE 7

| Properties | | CE1 | CE3 | CE2 | Ex1* | Ex2* | Ex3 |
|---|---|---|---|---|---|---|---|
| Flexural Strength acc. ISO6872 [MPa] | Mean | 1404 | 1363 | 1778 | 1766 | 1762 | 2124 |
| | Stdv | 162 | 114 | 132 | 159 | 181 | 148 |
| K1c SEVNB acc. ISO6872 [MPa*m$^{0.5}$] | Mean | 6.9 | 6.8 | 8.1 | 6.9 | 8.1 | 7.8 |
| | Stdv | 0.5 | 0.2 | 0.8 | 0.6 | 0.8 | 1.0 |

TABLE 7-continued

| Properties | CE1 | CE3 | CE2 | Ex1* | Ex2* | Ex3 |
|---|---|---|---|---|---|---|
| Monoclinic crystal phase content after 30 h in water vapor at 134° C., 2 bar [wt. %] | 57 | 19 | 90 | 41 | 40 | 42 |
| 3d printable via light curing | no | no | yes | yes | yes | yes |
| Castable via light curing | no | no | yes | yes | yes | yes |

Decreasing the yttria content and usage of Sol/Gel material generation technique resulted in an increased strength by around 374 MPa; compare CE1 vs. CE2.

Due to the reduced yttria content CE2 is less resistant against hydrothermal treatment as it shows a nearly complete transformation from tetragonal to monoclinic crystal phase (90 wt. %).

Adding alumina to CE2 increases the resistance against hydrothermal induced crystal phase transformation without decrease in flexural strength; compare CE2 to Ex1 and Ex2.

The value of monoclinic crystal phase content is lower compared to CE1 material which is already used as dental ceramic.

Further addition of alumina (Ex3) lead to a further increase of flexural strength compared to CE1 (+723 MPa) and Ex2 (+361 MPa).

FIG. 1 is an image of the microstructure of a sintered material based on the composition of CE1.

Figure 2:
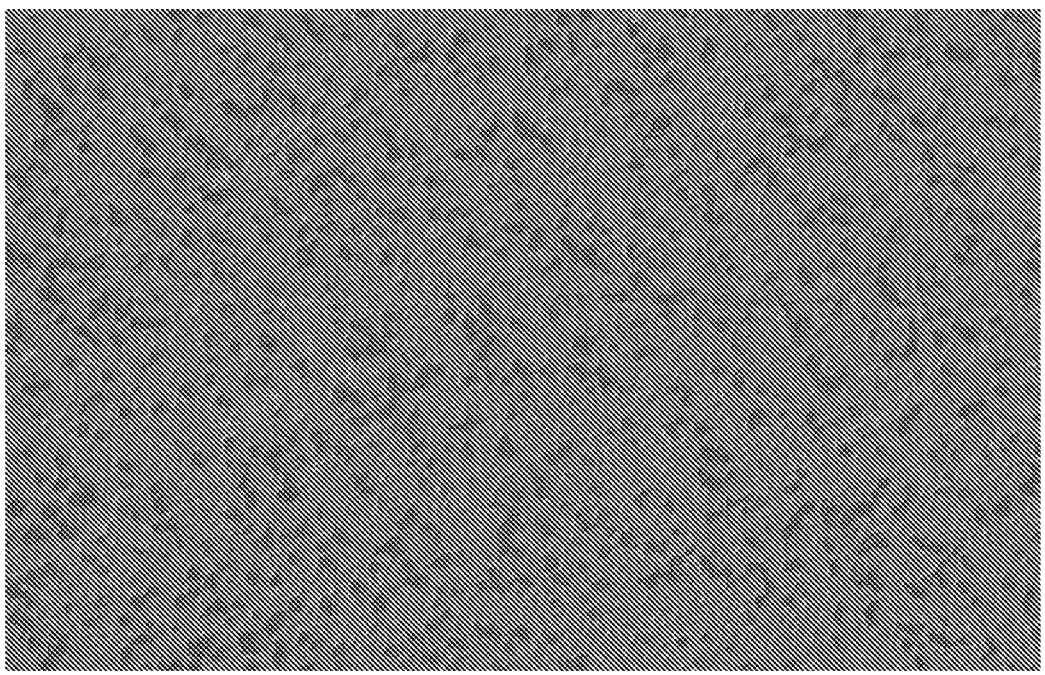
FIG. 2 shows the microstructure of a 2,2Y-TZP material with 12 wt. % alumina.

FIG. 2 is an image of the microstructure of a sintered material based on the composition of EX3.

The light grains relate to the yttria stabilized zirconia, whereas the darker grains relate to the second homogenously distributed alumina phase.

What is claimed is:

1. A sintered zirconia article comprising:
   $ZrO_2$: 80 to 87 wt. %,
   $Y_2O_3$: 3 to 5 wt. %, and
   $Al_2O_3$: 10 to 14 wt. %,
   wherein one or more of the zirconia and alumina has a grain size from 200 nm to 300 nm;
   the sintered zirconia article being characterized by a corundum crystal phase content of 7 to 12 wt. %, and
   the sintered zirconia article having a flexural strength of at least 2,000 MPa according to ISO 6872:2015;
   wherein wt. % is with respect to the weight of the sintered zirconia article.

2. The sintered zirconia article of claim 1, further being characterized by one or more of the following features:
   zirconia crystal phase content of tetragonal phase: more than 85 wt. %;
   zirconia crystal phase content of cubic phase: less than 2 wt. %; and
   zirconia crystal phase content of monoclinic phase: less than 2 wt. %.

3. The sintered zirconia article of claim 1, further being characterized by one or more of the following features:
   fracture toughness: at least 7 $MPa*m^{0.5}$ according to ISO 6872:2015;
   density: more than 98.5% with respect to theoretical density; and
   translucency: less than 20% determined on a polished sample having a thickness of 1 mm.

4. The sintered zirconia article claim 1, having the shape of a dental article, orthodontic article, or part thereof.

5. A process for producing a sintered zirconia article of claim 1, the process comprising:
   providing a porous zirconia article comprising:
      $ZrO_2$: 80 to 87 wt. %,
      $Y_2O_3$: 3 to 5 wt. %, and
      $Al_2O_3$: 10 to 14 wt. %,
      wherein wt. % is with respect to the weight of the porous zirconia article;
      the porous zirconia article being characterized by one or more of the following parameters:
         density: from 40 to 60% of theoretical density,
         average connected pore diameter: from 2 to 100 nm,
         BET surface: from 11 to 100 $m^2/g$, and
         Vickers hardness: from 10 to 100 HV1;
   providing a porous zirconia article by:
      providing a composition comprising:
         $ZrO_2$ in the term of inorganic oxide: 80 to 87 wt. %,
         $Y_2O_3$ in the term of inorganic oxide: 3 to 5 wt. %, and
         $Al_2O_3$ in the term of inorganic oxide: 10 to 14 wt. %,
         wherein wt. % is with respect to the weight of the composition;
      processing the composition by a casting technique or an additive manufacturing technique; and
      applying a calcining step; and
   applying a sintering step to obtain the sintered zirconia article,
   provided the process is free of a hot isostatic pressing step.

6. The sintered zirconia article of claim 1, further being characterized by one or more of the following features:
   fracture toughness: at least 7 $MPa*m^{0.5}$ according to ISO 6872:2015;
   density: more than 98.5% with respect to theoretical density; and
   translucency: less than 20% determined on a polished sample having a thickness of 1 mm.

7. The sintered zirconia article of claim 6, having the shape of a dental article, orthodontic article, or part thereof.

8. The process of claim 5, wherein the sintered zirconia article is further characterized by one or more of the following features:
   zirconia crystal phase content of tetragonal phase: more than 85 wt. %;
   zirconia crystal phase content of cubic phase: less than 2 wt. %; and
   zirconia crystal phase content of monoclinic phase: less than 2 wt. %.

9. The process of claim 5, wherein the sintered zirconia article is further characterized by one or more of the following features:
   fracture toughness: at least 7 $MPa*m^{0.5}$ according to ISO 6872:2015;
   density: more than 98.5% with respect to theoretical density; and
   translucency: less than 20% determined on a polished sample having a thickness of 1 mm.

* * * * *